US006316484B1

(12) United States Patent
Flygare et al.

(10) Patent No.: US 6,316,484 B1
(45) Date of Patent: Nov. 13, 2001

(54) PENTAFLUOROBENZENESULFONAMIDES AND ANALOGS

(75) Inventors: John A. Flygare, Burlingame; Julio Cesar Medina, Belmont; Bei Shan, Foster City; David Louis Clark, Albany; Terry J. Rosen, Burlingame, all of CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/633,740

(22) Filed: Aug. 7, 2000

Related U.S. Application Data

(63) Continuation of application No. 09/227,216, filed on Jan. 6, 1999, now Pat. No. 6,121,304, which is a continuation of application No. 08/896,827, filed on Jul. 18, 1997, now Pat. No. 5,880,151, which is a division of application No. 08/605,431, filed on Feb. 22, 1996, now abandoned.

(51) Int. Cl.[7] .................... C07D 409/00; C07D 295/00; C07D 265/30; C07D 211/08; C07C 311/00

(52) U.S. Cl. .................. 514/403; 514/238.8; 514/415; 514/518; 514/602; 514/604; 514/352; 544/166; 546/192; 548/361.1; 548/469; 558/56; 558/61; 564/90; 564/92

(58) Field of Search .................. 514/238.8, 403, 514/415, 518, 602, 604, 352; 544/166; 546/192; 548/361.1, 469; 558/56, 61; 564/90, 92

(56) References Cited

U.S. PATENT DOCUMENTS

| 1,955,207 | 4/1934 | Stotter et al. | 167/37 |
|---|---|---|---|
| 2,402,623 | 6/1946 | Hester | 260/554 |
| 3,034,955 | 5/1962 | Frick et al. | 167/37 |
| 4,881,969 | 11/1989 | Saupe et al. | 71/94 |
| 4,883,914 | 11/1989 | Alvarado et al. | 564/91 |
| 5,250,549 | 10/1993 | Yoshino et al. | 514/345 |

FOREIGN PATENT DOCUMENTS 469901  2/1992  (EP) .

OTHER PUBLICATIONS

Hawkinson et al., "Studies of solvolysis . . . ", *Journal of Organic Chemistry*, 53:(16) 3857–3860, 1988.

Shealy et al., "2–Haloethylating Agents for Cancer Chemotherapy, 2–Haloethyl Sulfonaes", *Journal of Medicinal Chemistry*, p. 1168–1173, (Aug. 6, 1983).

Olander et al., "A Study of the Binding of Two Sulfonamides to Carbonic Anhydrase", *Journal of American Chemical Society*, 95:(5) 1616–1621 (Mar. 7, 1973).

Fielding et al., "Synthesis and Reactions of 4–sulpho–2,3,5,6–tetrafluorobenzoic Acid.", *Journal of Florine Chemistry*, 59(1) 15–31 (Jan. 6, 1992).

Raibekas et al. "Affinity Probing of Flavin Binding Sites.2. Identification of reactive Cysteinr in the Flavin domain of Escherichia coli DNA Photolyase", *Biochemistry*, 33(42) 12656–12664 (Jan. 6, 1994).

*Primary Examiner*—Mukund J. Shah
*Assistant Examiner*—Tamthom N. Truong
(74) *Attorney, Agent, or Firm*—Townsend and Townsend and Crew LLP

(57) ABSTRACT

The invention provides methods and compositions relating to novel pentafluorophenylsulfonamide derivatives and analogs and their use as pharmacologically active agents. The compositions find particular use as pharmacological agents in the treatment of disease states, particularly atherosclerosis and hypercholesterolemia, or as lead compounds for the development of such agents. The compositions include compounds of the general formula I:

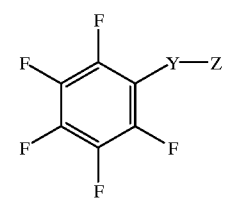

14 Claims, No Drawings

PENTAFLUOROBENZENESULFONAMIDES AND ANALOGS

This application is a continuation of application Ser. No. 09/227,216, filed Jan. 6, 1999, now U.S. Pat. No. 6,121,304, which is a continuation of 08/896,827, filed Jul. 18, 1997 now U.S. Pat. No. 5,880,151, which is a divisional of 08/605,431, filed Feb. 22, 1996 now abandoned the disclosures of each being incorporated by reference.

INTRODUCTION

1. Field of the Invention

The field of the invention is pentafluorobenzenesulfonamide derivatives and analogs their use as pharmacologically active agents.

2. Background

Atherosclerosis is a leading cause of death in the United States. The disease results from excess cholesterol accumulation in the arterial walls which forms plaques that inhibit blood flow and promote clot formation, ultimately causing heart attacks, stroke and claudication. The principal source of these cholesterol deposits are low-density lipoprotein (LDL) particles that are present in the blood. There is a direct correlation between LDL concentration and plaque formation in the arteries. LDL concentration is itself largely regulated by the supply of active LDL cell surface receptors which bind LDL particles and translocate them from the blood into the cell interior. Accordingly, the regulation of LDL receptor expression provides an importent therapeutic target.

Lipoprotein disorders have been previously called the hyperlipoproteinemias and defined as elevation of a lipoprotein level above normal. The hyperlipoproteinemias result in elevations of cholesterol, triglycerides or both and are clinically important because of their contribution to atherosclerotic diseases and pancreatitis.

Lipoproteins are spherical macromolecular complexes of lipid and protein. The lipid constituents of lipoproteins are esterified and unesterified (free) cholesterol, triglycerides, and phospholipids. Lipoproteins transport cholesterol and triglycerides from sites of absorption and synthesis to sites of utilization. Cholesteryl ester and triglycerides are nonpolar and constitute the hydrophobic core of lipoproteins in varying proportions. The lipoprotein surface coat contains the polar constituents—free cholesterol, phospholipids, and apolipoproteins—that permit these particles to be miscible in plasma.

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). The rate-limiting enzyme in endogenous cholesterol synthesis is 3-hydroxy-3-methylglutaryl coenzyme A (HMG-CoA) reductase. Triglycerides, which are nonpolar lipids consisting of a glycerol backbone and three fatty acids of varying length and degrees of saturation, are used for storage in adipose tissue and for energy. Lipoproteins are classified into groups based upon size, density, electrophoretic mobility, and lipid and protein composition. Very low density lipoproteins (VLDL) are large, triglyceride-rich lipoproteins that are synthesized and secreted by hepatocytes. VLDL interacts with lipoprotein lipase in capillary endothelium, and the core triglycerides are hydrolyzed to provide fatty acids to adipose and muscle tissue. About half of the catabolized VLDL particles are taken up by hepatic LDL receptors and the other half remain in plasma, becoming intermediate-density lipoprotein. IDL is enriched in cholesteryl ester relative to triglyceride and is gradually converted by hepatic triglyceride lipase to the smaller, denser, cholesterol ester-rich LDL. As IDL is converted to LDL, apolipoprotein E becomes detached, and only one apolipoprotein remains, apo B-100.

LDL normally carries about 75 percent of the circulating cholesterol. Cellular LDL uptake is mediated by a glycoprotein receptor molecule that binds to apo B-100. Approximately 70 percent of LDL is cleared by receptor uptake, and the remainder is removed by a scavenger cell pathway using nonreceptor mechanisms. The LDL receptors span the thickness of the cell's plasma membrane and are clustered in specialized regions where the cell membrane is indented to form craters called coated pits. These pits invaginate to form coated vesicles, where LDL is separated from the receptor and delivered to a lysosome so that digestive enzymes can expose the cholesteryl ester and cleave the ester bond to form free cholesterol. The receptor is recycled to the cell surface.

As free cholesterol liberated from LDL accumulates within cells, there are three important metabolic consequences. First, there is a decrease in the synthesis of HMG-CoA reductase, the enzyme that controls the rate of de novo cholesterol synthesis by the cell. Second, there is activation of the enzyme acyl cholesterol acyltransferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from the circulation.

Lipoproteins play a central role in atherogenesis. This association with the most common cause of death in the developed world defines the principal clinical importance of the hyperlipoproteinemias. Individuals with an elevated cholesterol level are at higher risk for atherosclerosis. Multiple lines of evidence, including epidemiological, autopsy, animal studies and clinical trials, have established that LDL is atherogenic and that the higher the LDL level, the greater the risk of atherosclerosis and its clinical manifestations. A certain level of LDL elevation appears to be a necessary factor in the development of atherosclerosis, although the process is modified by myriad other factors (e.g., blood pressure, tobacco use, blood glucose level, antioxidant level, and clotting factors), Acute pancreatitis is another major clinical manifestation of dyslipoproteinemia It is associated with chylomicronemia and elevated VLDL levels. Most patients with acute pancreatitis have triglyceride levels above 2,000 mg/dL, but a 1983 NIH consensus development conference recommended that prophylactic treatment of hypertriglyceridemia should begin when fasting levels exceed 500 mg/dL. The mechanism by which chylomicronenmia and elevated VLDL cause pancreatitis is unclear. Pancreatic lipase may act on triglyceride in pancreatic capillaries, resulting in the formation of toxic fatty acids that cause inflammation.

Abundant evidence indicates that treatment of hyperlipoproteinemia will diminish or prevent atherosclerotic complications. In addition to a diet that maintains a normal body weight and minimizes concentrations of lipids in plasma, therapeutic agents that lower plasma concentrations of lipoproteins, either by diminishing the production of lipoproteins or by enhancing the efficiency of their removal from plasma, are clinically important.

The most promising class of drugs currently available for the treatment of hyperlipoproteinemia or hypercholesterolemia acts by inhibiting HMG-CoA reductase, the rate-limiting enzyme in endogenous cholesterol synthesis. Drugs of this class competitively inhibit the activity of the enzyme. Eventually, this inhibition leads to a decrease in th endogenous synthesis of cholesterol and by normal homeostatic mechanisms, plasma cholesterol is taken up by LDL receptors to restore the intracellular cholesterol balance.

Through both the release of precursors of LDL and receptor-mediated LDL uptake from the serum, liver cells play a critical role in maintaining serum cholesterol homeostasis. In both man and animal models, an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesteryl esters, converted into bile acids and released into the bile duct, or enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element (SRE), appears to confer this sterol end product repression. This element has been extensively investigated (Brown, Goldstein and Russell, U.S. Pat. Nos. 4,745,060 and 4,935,363). The SRE can be inserted into genes that normally do not respond to cholesterol, conferring sterol end product repression of the chimeric gene. The exact mechanism of the repression is not understood. Brown and Goldstein have disclosed methods for employing the SRE in a screen for drugs capable of stimulating cells to synthesize LDL receptors (U.S. Pat. No. 4,935,363). It would be most desirable if the synthesis of LDL receptors could be upregulated at the level of gene expression. The upregulation of LDL receptor synthesis at this level offers the promise of resetting the level of serum cholesterol at a lower, and clinically more desirable, level. Presently, however, there are no cholesterol lowering drugs that are known to operate at the level of gene expression. The present invention describes methods and compounds that act to inhibit directly or indirectly the repression of the LDL receptor gene, resulting in induction of the LDL receptor on the surface of liver cells, facilitating LDL uptake, bile acid synthesis and secretion to remove cholesterol metabolites and hence the lowering of LDL-associated serun cholesterol levels.

Accordingly, it is one object of the present invention to provide compounds which directly or indirectly upregulate LDL receptor synthesis at the level of gene expression and are useful in the treatment of hypercholesterolemia or hyperlipoproteinemia.

A further object of the present invention is to provide therapeutic compositions for treating said conditions.

A further object of the invention is to provide therapeutic compositions for treating pancreatitis.

Still further objects are to provide methods for upregulating LDL receptor synthesis, for lowering senrm LDL cholesterol levels, and for inhibiting atherosclerosis.

Other objects, features and advantages will become apparent to those skilled in the art from the following description and claims.

SUMMARY OF THE INVENTION

The invention provides methods and compositions relating to novel pentafluorophenylsulfonamide derivatives and analogs and their use as pharmacologically active agents. The compositions find particular use as pharmacological agents in the treatment of disease states, particularly hypercholesterolemia and atherosclerosis, or as lead compounds for the development of such agents.

In one embodiment, the invention provides for the pharmaceutical use of compounds of the general formula I and for pharmaceutically acceptable compositions of compounds of formula I:

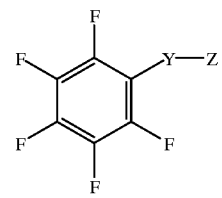

I or a physiologically acceptable salt thereof, wherein:

Y is —S(O)— or —S(O)$_2$—;

Z is —NR$^1$R$^2$ or —OR$^3$, where R$^1$ and R$^2$ are independently selected from hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl(C3–C8)cycloalkyl,
substituted or unsubstituted aryl-(C5–C7)cycloalkenyl,
substituted or unsubstituted aryloxy-(C3–C8) cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryloxy-(C2–C4) heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroalkyl,
substituted or unsubstituted heteroaryl-(C3–C6) alkenyl,
substituted or unsubstituted heteroaryloxy-(C1–C4) alkyl, and
substituted or unsubstituted heteroaryloxy-(C2–C4) heteroalkyl,
wherein R$^1$ and R$^2$ may be connected by a linking group E to give a substituent of the formula

wherein E represents a bond, (C1–C4) alkylene, or (C1–C4) heteroalkylene, and the ring formed by $R^1$, E, $R^2$ and the nitrogen contains no more than 8 atoms, or preferably the $R^1$ and $R^2$ may be covalently joined in a moiety that forms a 5- or 6-membered heterocyclic ring with the nitrogen atom of $NR^1R^2$; and where $R^3$ is a substituted or unsubstituted aryl or heteroaryl group.

Substituents for the alkyl, alkoxy, alkenyl, heteroalkyl, heteroalkenyl, alkynyl, cycloalkyl, heterocycloalkyl, cycloalkenylt, and cycloalkadienyl radicals are selected independently from —H
—OH
—O—(C1–C10)alkyl
=O
—$NH_2$
—NH—(C1–C10)alkyl
—N[(C1–C10)alkyl]$_2$
—SH
—S—(C1–C10)alkyl
—halo
—Si[(C1–C10)alkyl]$_3$ in a number ranging from zero to (2N+1), where N is the total number of carbon atoms in such radical.

Substituents for the aryl and heteroaryl groups are selected independently from

—halo
—OH
—O—R'
—O—C(O)—R'
—$NH_2$
—NHR'
—NR'R"
—SH
—SR'
—R'
—CN
—$NO_2$
—$CO_2H$
—$CO_2$—R'
—$CONH_2$
—CONH—R'
—CONR'R"
—O—C(O)—NH—R'
—O—C(O)—NR'R"
—NH—C(O)—R'
—NR"—C(O)—R'
—NH—C(O)—OR'
—NR"—C(O)—R'
—NH—C($NH_2$)=NH
—NR'—C($NH_2$)=NH
—NH—C($NH_2$)=NR'
—S(O)—R'
—S(O)$_2$—R'
—S(O)$_2$—NH—R'
—S(O)$_2$—NR'R"
—$N_3$
—CH(Ph)$_2$
substituted or unsubstituted aryloxy
substituted or unsubstituted arylamino
substituted or unsubstituted heteroarylamino
substituted or unsubstituted heteroaryloxy
substituted or unsubstituted aryl-(C1–C4)alkoxy,
substituted or unsubstituted heteroaryl-(C1–C4)alkoxy,
perfluoro(C1–C4)alkoxy, and
perfluoro(C1–C4)alkyl, in a number ranging from zero to the total number of open valences on the aromatic ring system;

and where R' and R"are independently selected from:
substituted or unsubstituted (C1–C10)alkyl,
substituted or unsubstituted (C1–C10)heteroalkyl,
substituted or unsubstituted (C2–C6)alkenyl,
substituted or unsubstituted (C2–C6)heteroalkenyl,
substituted or unsubstituted (C2–C6)alkynyl,
substituted or unsubstituted (C3–C8)cycloayl,
substituted or unsubstituted (C3–C8)heterocycloalkyl,
substituted or unsubstituted (C5–C6)cycloalkenyl,
substituted or unsubstituted (C5–C6)cycloalkadienyl,
substituted or unsubstituted aryl,
substituted or unsubstituted aryl-(C1–C4)alkyl,
substituted or unsubstituted aryl-(C1–C4)heteroalkyl,
substituted or unsubstituted aryl-(C2–C6)alkenyl,
substituted or unsubstituted aryloxy-(C1–C4)alkyl,
substituted or unsubstituted aryloxy-(C1–C4)heteroalkyl,
substituted or unsubstituted heteroaryl,
substituted or unsubstituted heteroaryl-(C1–C4)alkyl,
substituted or unsubstituted heteroayl-(C1–C4) heteroalkyl,
substituted or unsubstituted heteroaryl-(C2–C6)alkenyl,
substituted or unsubstituted heteroaryloxy-(C1–C4)alkyl, and
substituted or unsubstituted heteroaryloxy-(C1–C4) heteroalkyl.

Two of the substituents on adjacent atoms of the aryl or heteroaryl ring may optionally be replaced with a substituent of the formula —T—C(O)—(CH$_2$)$_n$—U—, wherein T and U are independently selected from N, O, and C, and n=0–2. Alternatively, two of the substituents on adjacent atoms of the aryl or heteroaryl ring may optionally be replaced with a substituent of the formula —A—(CH2)p—B—, wherein A and B are independently selected from C, O, N, S, SO, SO$_2$, and SO$_2$NR', and p=1–3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_q$—X—(CH$_2$)$_r$—, where q and r are independently 1–3, and X is selected from O, N, S, SO, SO$_2$ and SO$_2$NR'. The substituent R' in SO$_2$NR' is selected from hydrogen or (C1–C6)alkyl.

In another embodiment, the invention provides novel methods for the use of pharmaceutical compositions containing compounds of the foregoing description of the general formula I. The invention provides novel methods for treating pathology such as hypercholesterolernia, atherosclerosis, pancreatitis, and hyperlipoproteinemia, including administering to a patient an effective formulation of one or more of the subject compositions.

In another embodiment, the invention provides chemically-stable, pharmacologically active compounds of general formula I:

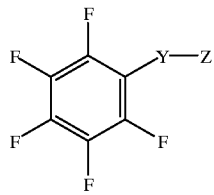

I or a pharmaceutically acceptable salt thereof, wherein:
Y is —S(O)— or —S(O$_2$)—; and
Z is NR$^1$R$^2$, wherein R$^2$ is an optionally substituted aryl or heteroaryl group, and R$^1$ is selected from:
hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8) cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryloxy-(C2–C4) heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroyl,
substituted or unsubstituted heteroaryl-(C3–C6) alkenyl,
substituted or unsubstituted heteroaryloxy-(C1–C4) alkyl, and
substituted or unsubstituted heteroaryloxy-(C2–C4) heteroalkyl,
wherein R$^1$ and R$^2$ may be connected by a linking group E to give a substituent of the formula

wherein E represents a bond, (C1–C4) alxylene, or (C1–C4) heteroalkylene, and the ring formed by R$^1$, E, R$^2$ and the nitrogen contains no more than 8 atoms, or preferably the R$^1$ and R$^2$ may be covalently joined in a moiety that forms a 5- or 6-membered heterocyclic ring with the nitrogen atom of NR$^1$R$^2$;
provided that:
in the case that Y is —S(O$_2$)—, and R$^1$ is hydrogen or methyl, then R$^2$ is substituted pheny or heteroaryl group;
in the case that Y is —S(O$_2$)— and R$^2$ is a ring system chosen from 1-naphthyl, 5-quinolyl, or 4-pyridyl, then either R$^1$ is not hydrogen or R$^2$ is substituted by at least one substituent that is not hydrogen;
in the case that Y is —S(O$_2$)—, R$^2$ is phenyl, and R$^1$ is a propylene unit attaching the nitrogen of —NR$^1$R$^2$— to the 2-position of the phenyl ring in relation to the sulfonamido group to form a 1,2,3,4-tetrahydroquinoline system, one or more of the remaining valences on the bicyclic system so formed is substituted with at least one substituent that is not hydrogen;
in the case that Y is —S(O$_2$)— and R$^2$ is phenyl substituted with 3-(1-hydroxyethyl), 3-dimethylamino, 4-dimethylamino, 4-phenyl, 3-hydroxy, 3-hydroxy-4-diethylaminomethyl, 3,4-methylenedioxy, 3,4-ethylenedioxy, 2-(1-pyrrolyl), or 2-methoxy-4-(1-morpholino), then either R$^1$ is not hydrogen or when R$^1$ is hydrogen, one or more of the remaining valences on the phenyl ring of R$^2$ is substituted with a substituent that is not hydrogen;
in the case that Y is —S(O$_2$)— and R$^2$ is 2-methylbenzothiazol-5-yl, 6-hydroxy-4-methyl-pyrmidin-2-yl, 3-carbomethoxypyrazin-2-yl, 5-carbomethoxypyrazin-2-yl, 4-carboethoxy-1-phenylpyrazol-5-yl, 3-methylpyrazol-5-yl, 4chloro-2-methylthiopyrimidin-6-yl, 2-trifluoromethyl-1,3,4-thiadiazol-5-yl, 5,6,7,8-tetrahydro-2-naphthyl, 4-methylthiazol-2-yl, 6,7-dihydroindan-5-yl, 7-chloro-5-methyl-1,8-naphthyridin-2-yl, 5,7-dimethyl-1,8-naphthyridin-2-yl, or 3-cyanopyrazol-4-yl, R$^1$ is a group other than hydrogen.

DETAILED DESCRIPTION OF THE INVENTION

The term "alkyl" by itself or as part of another substituent means, unless otherwise stated, a straight or branched chain hydrocarbon radical, including di- and multi-radicals, having the number of carbon atoms designated (i.e. C1–C10 means one to ten carbons) and includes straight or branched chain groups such as methyl, ethyl, n-propyl, isopropyl, n-butyl, t-butyl, isobutyl, sec-butyl, homologs and isomers of n-pentyl, n-hexyl, 2-methylpentyl, 1,5-dimethylhexyl, 1-methyl-4-isopropylhexyl and the like. The term "alkylene" by itself or a part of another substituent means a divalent radical derived from an alkane, as exemplified by —CH$_2$CH$_2$CH$_2$CH$_2$—. A "lower alkyl" is a shorter chain alkyl, generally having six or fewer carbon atoms.

The term "heteroalkyl" by itself or in combination with another term means, unless otherwise stated, a stable straight or branched chain radical consisting of the stated number of carbon atoms and one or two heteroatoms selected from the group consisting of O, N, and S, a wherein the nitrogen and sulfiur atoms may optionally be oxidized and the nitrogen heteroatom may optionally be quaternized. The heteroatom (s) may be placed at any position of the heteroalkyl group, including between the rest of the heteroalkyl group and the fragment to which it is attached, as well as attached to the most distal carbon atom in the heteroalkyl group. Examples include —O—CH$_2$—CH$_2$—CH$_3$, —CH$_2$—CH$_2$—O—CH$_3$, —CH$_2$—CH$_2$—CH$_2$—OH, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —O—CH$_2$—CH$_2$—CH$_2$—NH—CH$_3$, and —CH$_2$—CH$_2$—S(O)$_2$—CH$_3$. Up to two heteroatoms may be consecutive, such as, for example, —CH$_2$—NH—OCH$_3$. The term "heteroalkylene" by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—.

The terms "cycloalkyl" and "heterocycloalkyl", by themselves or in combination with other terms, represent, unless otherwise stated, cyclic versions of "alkyl" and "heteroalkyl", respectively. Examples of cycloalkyl include cyclopentyl, cyclohexyl, cycloiieptyl, and the like. Examples of heterocycloalkyl include 1-piperidinyl, 2-piperidinyl, 3-piperidinyl, 4-morpholinyl, 3-morpholinyl, tetmahydrofiran-2-yl, tetrahydrofliran-3-yl, tetrahydrothien-2-yl, tetrahydrothien-3-yl, 1-piperazinyl, 2-piperazinyl, and the like.

The term "alkenyl" employed alone or in combination with other terms, means, unless otherwise stated, a stable straight chain or branched monounsaturated or diunsaturated hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A divalent radical derived from an alkene is exemplified by —CH=CH—CH$_2$—.

The term "heteroalkenyl" by itself or in combination with another term means, unless otherwise stated, a stable straight or branched chain monounsaturated or diunsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

The term "alkynyl" employed alone or in combination with other terms, means, unless otherwise stated, a stable straight chain or branched hydrocarbon group having the stated number of carbon atoms, and containing one or two carbon-carbon triple bonds, such as ethynyl, 1- and 3-propynyl, 4-but-1-ynyl, and the higher homologs and isomers.

The term "alkoxy" employed alone or in combination with other terms, means, unless otherwise stated, an alkyl group, as defined above, connected to the rest of the molecule via an oxygen atom, such as, for example, methoxy, ethoxy, 1-propoxy, 2-propoxy and the higher 30 homologs and isomers.

The terms "halo" or "halogen" by themselves or as part of another substituent mean, unless otherwise stated, a fluorine, chlorine, bromine, or iodine atom.

The term "aryl" employed alone or in combination with other terms, means, unless otherwise stated, a phenyl, 1-naphthyl, or 2-naphthyl group. The maximal number of substituents allowed on each one of these ring systems is five, seven, and seven, respectively. Substituents are selected from the group of acceptable substituents listed above.

The term "heteroaryl" by itself or as part of another substituent means, unless otherwise stated, an unsubstituted or substituted, stable, mono- or bicyclic heterocyclic aromatic ring system which consists of carbon atoms and from one to four heteroatoms selected from the group consisting of N, O, and S, and wherein the nitrogen and sulfir heteroatoms may optionally be oxidized, and the nitrogen atom may optionally be quaternized. The heterocyclic system may be attached, unless otherwise stated at any heteroatom or carbon atom which affords a stable structure. The heterocyclic system may be substituted or unsubstituted with one to four substituents independently selected from the list of acceptable aromatic substituents listed above. Examples of such heterocycles include 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrinidyl, 5-benzothiazolyl, purinyl, 2-benzimidazolyl, 5-indolyl, 1-isoquinolyl, 5-isoquinolyl, 2quinoxalinyl, 5-quinoxalinyl, 3-quinolyl, and 6-quinolyl.

Pharmaceutically acceptable salts of the compounds of Formula I include salts of these compounds with relatively nontoxic acids or bases, depending on the particular substituents found on specific compounds of Formula I. When compounds of Formula I contain relatively acidic functionalities, base addition salts can be obtained by contacting the neutral form of compound I with a sufficient amount of the desired base, either neat or in a suitable inert solve Examples of pharmaceutically acceptable base addition salts include sodium, potassium, calcium, ammonium, organic amino, or magnesium salt, or a similar salt. When compounds of Formula I contain relatively basic functionalities, acid addition salts can be obtained by contacting the neutral form of compound I with a sufficient amount of the desired acid, either neat or in a suitable inert solvent. Examples of pharmaceutically acceptable acid addition salts include those 30 derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like gluconic or galactunoric acids and the like (see, for example, Berge, S. M., et al, "Pharmaceutical Salts", *Journal of Pharmnaceutical Science*, Vol. 66, pages 1–19 (1977)). Certain specific compounds of Formula I contain both basic and acidic functionalities that allow the compounds to be converted into either base or acid addition salts.

The free base form may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention possess asymmetric carbon atoms (optical centers); the racemates, diastereomers, and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$) or carbon-14 ($^{14}C$). All isotopic variations of the compounds of the present invention, whether radioactive or not, are intended to be encompassed within the scope of the present invention.

In various preferred embodiments of the pharmaceutical compositions of compounds of formula I, Y is $S(O_2)$ and Z is $NR^1R^2$, wherein $R^1$ is hydrogen or methyl, and $R^2$ is a substituted phenyl, preferably mono-, di-, or trisubstituted as follows. In one group of preferred compounds, Y is $S(O_2)$ and Z is $NR^1R^2$, wherein $R^1$ is hydrogen or methyl, and $R^2$ is a phenyl group, preferably substituted in the para position by one of the following groups: hydroxy, amino, (C1–C10) alkoxy. (C1–C10)alkyl, (C1–C10)alkylamino, and [di (C1–C10)alkyl]amino, with up to four additional substituents independently chosen from hydrogen, halogen, (C1–C10)alkoxy, (C1–C10)alkyl, and [di(C1–C10)alkyl] amino. Also preferred are compounds of formula I where there is no linking group E between $R^1$ and $R^2$.

Illustative examples of pharmaceutical compositions and compounds of the subject pharmaceutical methods include:
3-Fluoro-4-methoxy-1-pentafluorophenylsulfmamidobenzene;
4-Dimethylamino-1-pentafluorophenylsulfiiamidobenzene;
4Methyl-6-methoxy-2-pentafluorophenylsulfonamidopyrimidine;
4,6-Dimethoxy-2-pentafluorophenylsulfonamidopyrimidine;
2-Pentafluorophenylsulfonamidothiophene;
3-Pentafluorophenylsulfonamidothiophene;
3-Pentafluorophenylsulfonamidopyridine;
4-Pentafluorophenylsulfonamidopyridine;
4-(N,N,-Dimethylamino)-1-(Nethylpentafluorophenylsulfonamido)-benzene;
4-tert-Butoxy-1-pentafluorophenylsulfonamidobenzene;
3-tert-Butoxy-1-pentafluorophenylsulfonamidobenzene;
2-tert-Butoxy-1-pentafluorophenylsulfonamidobenzene;
4-Isopropoxy-1-pentafluorophenylsulfonamidobenzene;
3-Isopropoxy-1-pentafluorophenylsulfonamidobenzene;
2-Isopropoxy-1-pentafluorophenylsulfonamidobenzene;
2-Methoxy-1,3-difluoro-5-pentafluorophenylsulfonamidobenzene;
4-Cyclopropoxy-1-pentafluorophenylsulfonamidobenzene;
3-Fluoro-4yclopropoxy-1-pentafluorophenylsulfonamidobenzene;
3-Hydroxy4-cyclopropoxy-1-pentafluorophenylsulfonamidobenzene;
1-Hydroxy-2,3-methylenedioxy-5-pentafluorophenylsulfonamidobenzene;
1-Hydroxy-2,3-ethylenedioxy-5-pentafluorophenylsulfonamidobenzene;
1-Hydroxy-2,3-carbodioxy-5-pentafluorophenylsulfonamidobenzene;
1,3-Dihydroxy-2ethoxy-5-pentafluorophenylsulfonamidobenzene;
1-Pentafluorophenylsulfonylindole;
1-Pentafluorophenylsulfonyl(2,3-dihydro)indole;
1-Pentafluorophenylsulfonyl(1,2-dihydro)quinoline;
1-Pentafluorophenylsulfonyl(1,2,3,4-tetrahydro)quinoline;
3,4-Difluoro-1-pentafluorophenylsulfonamidobenzene;
4-Trifluoromethoxy-1-pentafluorophenylsulfonamidobenzene;
2-Chloro-5-pentafluorophenylsulfonamidopyridine;
2-Hydroxy-1-methoxy-4-[N-5-hydroxypent-1-yl) pentafluorophenyl-sulfonamido]benzene;
4-(1,1-Dimethyl)ethoxy-1-pentafluorophenylsulfonamidobenzene;
1-Bromo-3-hydroxy4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
3-Chloro-1-pentafluorophenylsulfonamidobenzene;
4-Chloro-1-pentafluorophenylsulfonamidobenzene;
3-Nitro-1-pentafluorophenylsulfonamidobenzene;
4-Methoxy-1-pentafluorophenylsulfonamido-3-trifluoromethyl)benzene;
4-Methoxy-1-[N-(2-propenyl) pentafluorophenylsulfonamido]benzene;
1-(N-(3-Butenyl)pentafluorophenylsulfonamido)-4-methoxybenzene;
4-Methoxy-1-(N-(4-pentenyl) pentafluorophenylsulfonamido)benzene;
1-[N-(2,3-Dihydroxypropy,) pentafluorophenylsulfonamido]-4-methoxy-benzene;
1-(N-(3,4-Dihydroxybutyl)pentafluorophenylsulfonamido)-4-methoxybenzene;
1-(N-(4,5-Dihydroxypentyl) pentafluorophenylsulfonamido)-4-methoxybenzene;
1-(N-(4-hydroxybutyl)pentafluorophenylsulfonamido)4-methoxybenzene;
4-Methoxy-1-(N-(5-hydroxypentyl) pentafluorophenylsulfonamido)-benzene;
3-Amino-4-methoxy-1-pentafluorophenylsulfonamidobenzene;
4-Butoxy-1-pentafluorophenylsulfonamidobenzene;
1-Pentafluorophenylsulfonamido-4-phenoxybenzene;
6-Pentafluorophenylsulfonamidoquinoline;
2,3-Dihydro-5-pentafluorophenylsulfonamidindole;
5-Pentafluorophenylsulfonamidobenzo[a]thiophene;
5-Pentafluorophenylsulfonamidobenzo[a]furan;
3-Hydroxy4-(1-propenyl)-1-pentafluorophenylsulfonamidobenzene;
4-Benzyloxy-1-pentafluorophenylsulfonamidobenzene;
4-Methylmercapto-1-pentafluorophenylsulfonamidobenzene;
2-Methoxy-1-pentafluorophenylsulfonamidobenzene;
4-Allyloxy-1-pentafluorophenylsulfonamidobenzene;
1-Pentafluorophenylsulfonamido-4-propoxybenzene;
4(1-Methyl)ethoxy-1-pentafluorophenylsulfonamidobenzene;
1,2-Methylenedioxy-4-pentafluorophenylsulfonamidobenzene;
1,2-Dimethoxy-4-peniafluorophenylsulfonamidobenzene;
4-(N,N-Diethylamino)-1-pentafluorophenylsulfonarmidobenzene;
4-Amino-1-pentafluorophenylsulfoniamidobenzene;
Pentafluorophenylsulfonamidobenzene;
5-Pentafluorophenylsulfonamidoindazole;
4-(N,N-Dimethylamino)-1-(N-methylpentafluorophenylsulfonamido)-benzene;
1,2-Dihydroxy-4-pentafluorophenylsulfonamidobenzene;
3,5-Dimethoxy-1-pentafluorophenylsulfonamidobenzene;
3-Ethoxy-1-pentafluorophenylsulfonamidobenzene;
7-Hydroxy-2-pentafluorophenylsulfonamidonaphthalene;
3-Phenoxy-1-pentafluorophenylsulfonamidobenzene;
4-(1-Morpholino)-1-pentafluorophenylsulfonamidobenzene;

5-Pentafluorophenylsulfonamido-1,2,3-trimethoxybenzene;
2-Hydroxy-1,3-methoxy-5-pentafluorophenylsulfonamidobenzene;
1,2-Dihydroxy-3-methoxy-5-pentafluorophenylsulfonamidobenzene;
5-Pentafluorophenylsulfonamido-1,2,3-trihydroxybenzene;
3-Hydroxy-5-methoxy-1-pentafluorophenylsulfonamidobenzene;
3,5-Dihydroxy-1-pentafluorophenylsulfonamidobenzene;
2-Fluoro-1-methoxy-4-(N-methylpentafluorophenylsulfonamido)benzene;
4-(N,N-Dimethylamino)-1-pentafluorophenylsulfonamidobenzene, hydrochloride;
2-Methoxy-5-pentafluorophenylsulfonamidopyridine; and
2-Anilino-3-pentafluorophenylsulfonamidopyridine.

Examples of the most preferred pharmaceutical compositions and compounds of the subject pharmaceutical methods include:
4-(N,N-Dimethylamino)-1-pentafluorophenylsulfonamidobenzene;
3-(N,N-Dimethylamino)-1-pentafluorophenylsulfonamidobenzene;
1,2-Ethylenedioxy-4-pentafluorophenylsulfonamidobenzene;
2-Hydroxy-1-methoxy-4-pentafluorophenylsulfonamidobenzene;
2-Fluoro-1-methoxy-4-pentafluorophenylsulfonamidobenzene;
2-Hydroxy-1-methoxy-4-pentafluorophenylsulfonamidobenzene, sodium salt;
2-Hydroxy-1-methoxy-4-pentafluorophenylsulfonamidobenzene, potassium salt;
2-Fluoro-1-methoxy-4-pentafluorophenylsulfonaraidobenzene, sodium salt;
2-Fluoro-1-methoxy-4-pentafluorophenylsulfonamidobenzene, potassium salt;
4-Methoxy-1-pentafluorophenylsulfonamidobenzene;
3-Hydroxy-1-pentafluorophenylsulfonamidobenzene;
4-Hydroxy-1-pentafluorophenylsulfonamidobenzene;
1,2-Dimethyl-4-pentafluorophenylsulfonamidobenzene;
5-Pentafluorophenylsulfonamidoindole;
4-Ethoxy-1-pentafluorophenylsulfonamidobenzene;
3-Methoxy-1-pentafluorophenylsulfonamidobenzene;
2-Bromo-1-methoxy-4-pentafluorophenylsulfonamidobenzene;
2-Chloro-1-methoxy-4-pentafluorophenylsulfonamidobenzene;
2-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
4-Chloro-1-pentafluorophenylsulfonamidobenzene; and
3-Amino-4-methoxy-2-pentafluorophenylsulfonamidobenzene.

The invention provides for certain novel compounds of general Formula I that possess one or more valuable biological activities such as a pharmacologic, toxicologic, metabolic, etc. Exemplary compounds of this embodiment of the invention include:
2-Fluoro-1-methoxy-4-pentafluorophenylsulfmamidobenzene;
4-Dimethylamino-1-pentafluorophenylsulfmamidobenzene;
4-Methyl-6-methoxy-2-pentafluorophenylsulfonamidopyrimidine;
4,6-Dimethoxy-2-pentafluorophenylsulfonamidopyrimidine;
2-Pentafluorophenylsulfonamidothiophene;
3-Pentafluorophenylsulfonamidothiophene;
3-Pentafluorophenylsulfonamidopyridine;
4-Pentafluorophenylsulfonamidopyridine;
4-(N,N,-Dimethylamino)-1-(N-ethylpentafluorophenylsulfonamido) benzene;
4-tert-Butoxy-1-pentafluorophenylsulfonamidobenzene;
3-tert-Butoxy-1-pentafluorophenylsulfonamidobenzene;
2-tert-Butoxy-1-pentafluorophenylsulfonamidobenzene;
4-Isopropoxy-1-pentafluorophenylsulfonamidobenzene;
3-Isopropoxy-1-pentafluorophenylsulfonamidobenzene;
2-Isopropoxy-1-pentafluorophenylsulfonamidobenzene;
2-Methoxy-1,3-difuoro-5-pentafluorophenylsulfonamidobenzene;
1-Hydroxy-2,3-methylenedioxy-5-pentafluorophenylsulfonamidobenzene;
1-Hydroxy-2,3-ethylenedioxy-5-pentafluorophenylsulfonamidobenzene;
1-Hydroxy-2,3-cabodioxy-5-pentafluorophenylsulfonamidobenzene;
1,3-Dihydroxy-2-ethoxy-5-pentafluorophenylsulfonamidobenzene;
1-Pentafluorophenylsulfonylindole;
1-Pentafluorophenylsulfonyl(2,3-dihydro)indole;
1-Pentafluorophenylsulfonyl(1,2,-dihydro)quinoline;
1-Pentafluorophenylsulfonyl(1,2,3,4-tetrahydro)quinoline;
3,4-Difluoro-1-pentafluorophenylsulfonamidobenzene;
4-Trifluoromethoxy-1-pentafluorophenylsulfonamidobenzene;
2-Chloro-5-pentafluorophenylsulfonamidopyridine;
2-Hydroxy-1-methoxy-4-[N-5-hydroxypent-1-yl)pentafluorophenyl-sulfonamido]benzene;
4-(1,1-Dimethyl)ethoxy-1-pentafluorophenylsulfonamidobenzene;
1-Bromo-3-hydroxy-4-methoxy-1-pentafluorophenylsulfonamidobenzene;
2-Bromo4-methoxy-5-hydroxy-1-pentafluorophenylsulfonamidobenzene;
1-Bromo-4-fluoro-5-methoxy-2-pentafluorophenylsulfonamidobenzene;
3-Chloro-1-pentafluorophenylsulfonarnidobenzene;
4-Chloro-1-pentafluorophenylsulfonarnidobenzene;
3-Nitro-1-pentafluorophenylsulfonamidobenzene;
4-Methoxy-1-pentafluorophenylsulfonamido-3-(trifluoromethyl)benzene;
4-Methoxy-1-[N-(2-propenyl)pentafluorophenylsulfonamido]benzene;
1-(N-(3-Butenyl)pentafluorophenylsulfonamido)-4-methoxybenzene;
4-Methoxy-1-(N-(4-pentenyl)pentafluorophenylsulfonamido)benzene;
1-[(N-(2,3-Dihydroxypropyl)pentafluorophenylsulfonamido]-4-methoxy-benzene;
1-(N-(3,4-Dihydroxybutyl)pentafluorophenylsulfonamido)-4-methoxybenzene;
1-(N-(4,5-Dihydroxypentyl)pentafluorophenylsulfonamido)-4-methoxybenzene;
1-(N-(4-hydroxybutyl)pentafluorophenylsulfonamido)-4-methoxybenzene;
4-Methoxy-1-(N-(5-hydroxypentyl)pentafluorophenylsulfonamido)-benzene;
3-Amino-4-methoxy-1-pentafluorophenylsulfonamidobenzene;
4-Butoxy-1-pentafluorophenylsulfonamidobenzene;
1-Pentafluorophenylsulfonamido-1-phenoxybenzene;
4-Benzyloxy-1-pentafluorophenylsulfonamidobenzene;
4-Methylmercapto-1-pentafluorophenylsulfonamidobenzene;

2-Methoxy-1-pentafluorophenylsulfonamidobenzene;
4-Allyloxy-1-pentafluorophenylsulfonamidobenzene;
1-Pentafluorophenylsulfonamido-4-propoxybenzene;
4-(1-Methyl)ethoxy-1-pentafluorophenylsulfonamidobenzene;
1,2-Methylenedioxy-4-pentafluorophenylsulfonamidobenzene;
1,2-Dimethoxy-4-pentafluorophenylsulfonamidobenzene;
4-(N,N-Diethylamino)-1-pentafluorophenylsulfonamidobenzene;
4-Amino-1-pentafluorophenylsulfonamidobenzene;
Pentafluorophenylsulfonamidobenzene;
5-Pentafluorophenylsulfonamidoindazole;
4-(N,N-Dimethylamino)-1-(N-methylpentafluorophenylsulfonamido)-benzene;
1,2-Dihydroxy-4-pentafluorophenylsulfonamidobenzene;
3,5-Dimethoxy-1-pentafluorophenylsulfonamidobenzene;
3-Ethoxy-1-pentafluorophenylsulfonamidobenzene;
7-Hydroxy-2-pentafluorophenylsulfonamidonaphthalene;
3-Phenoxy-1-pentafluorophenylsulfonamidobenzene;
4-(1-Morpholino)-1-pentafluorophenylsulfonamidobenzene;
5-Pentafluorophenylsulfonamido-1,2,3-trimethoxybenzene;
2-Hydroxy-1,3-methoxy-5-pentafluorophenylsulfonamidobenzene;
1,2-Dihydroxy-3-methoxy-5-pentafluorophenylsulfonamidobenzene;
5-Pentafluorophenylsulfonamido-1,2,3-trihydroxybenzene;
4-Cyclopropoxy-1-pentafluorophenylsulfonamidobenzene;
3-Fluoro-4-cyclopropoxy-1-pentafluorophenylsulfonamidobenzene;
6-Pentafluorophenylsulfonamidoquinoline;
2,3-Dihydro-5-pentafluorophenylsulfonamidoindole;
5-Pentafluorophenylsulfonamidobenzo[a]thiophene;
5-Pentafluorophenyisulfonamidobenzo[a]furan;
3-Hydroxy-4-(1-propenyl)-1-pentafluorophenylsulfonamidobenzene;
3-Hydroxy-5-methoxy-1-pentafluorophenylsulfonamidobenzene;
3,5-Dihydroxy-1-pentafluorophenylsulfonamidobenzene;
2-Fluoro-1-methoxy-4-(N-methylpentafluorophenylsulfonamido)benzene;
4(N,N-Dimethylamino)-1-pentafluorophenylsulfonamidobenzene, hydrochloride; and,
2-Analino-3-pentafluorophenylsulfonamidopyridine.

Preferred compounds of this embodiment of the invention have specific pharmacological properties. Examples of the most preferred compounds of this embodiment of the invention include:
4-(N,N-Dimethylamino)-1-pentafluorophenylsulfonamidobenzene;
3-(N,N-Dimethylamino)-1-pentafluorophenylsulfonamidobenzene;
1,2-Ethylenedioxy-4-pentafluorophenylsulfonamidobenzene;
2-Hydroxy-1-methoxy-4-pentafluorophenylsulfonamidobenzene;
2-Fluoro-1-methoxy-4-pentafluorophenylsulfonamidobenzene;
2-Hydroxy-1-methoxy-4-pentafluorophenylsulfonamidobenzene, sodium salt;
2-Hydroxy-1-methoxy-4-pentafluorophenylsulfonamidobenzene, potassium salt;
2-Fluoro-1-methoxy-4-pentafluorophenylsulfonamidobenzene, sodium salt;
2-Fluoro-1-methoxy-4-pentafluorophenylsulfonamidobenzene, potassium salt;
4-Methoxy-1-pentafluorophenylsulfonamidobenzene;
3-Hydroxy-1-pentafluorophenylsulfonamidobenzene;
4-Hydroxy-1-pentafluorophenylsulfonamidobenzene;
1,2-Dimethyl-4-pentafluorophenylsulfonamidobenzene;
5-Pentafluorophenylsulfonamidoindole;
4-Ethoxy-1-pentafluorophenylsulfonamidobenzene;
3-Methoxy-1-pentafluorophenylsulfonamidobenzene;
2-Bromo-1-methoxy-4-pentafluorophenylsulfonamidobenzene;
2-Chloro-1-methoxy-4-pentafluorophenylsulfonamidobenzene;
2-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
4-Chloro-1-pentafluorophenylsulfonamidobenzene; and
3-Amino-4-methoxy-1-pentafluorophenylsulfonamidobenzene.

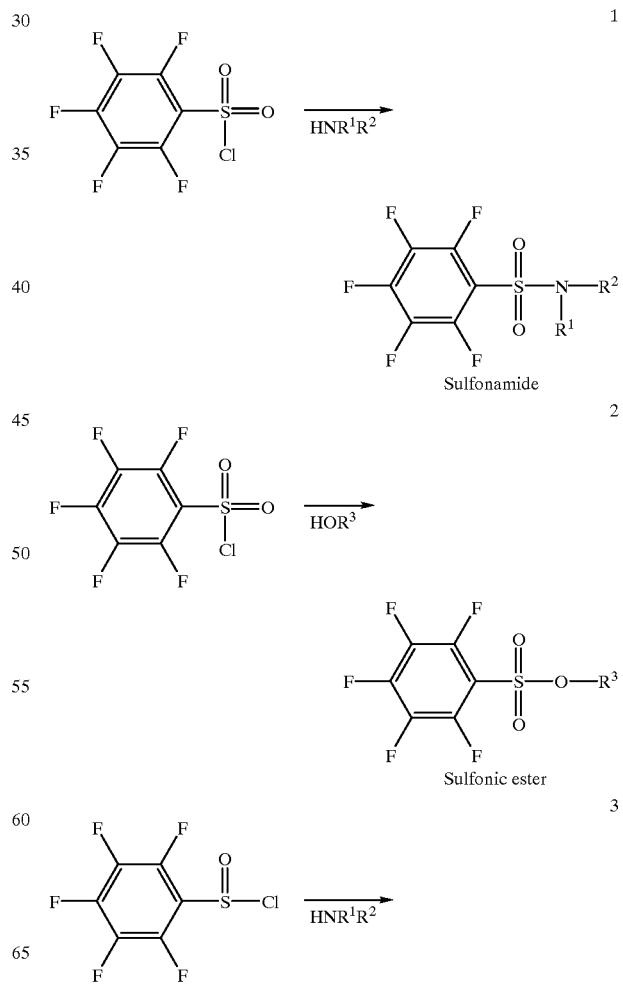

Scheme I
Syntheses of pentafluorophenylsulfonamides, sulfonic esters, sulfinamides and sulfinic esters

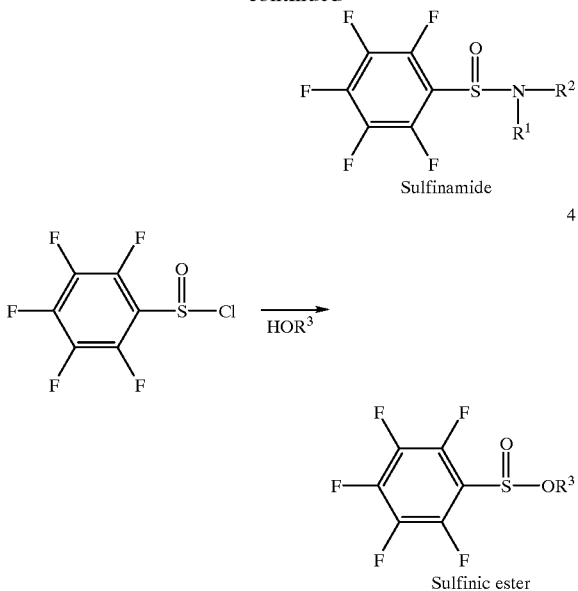

Sulfinamide

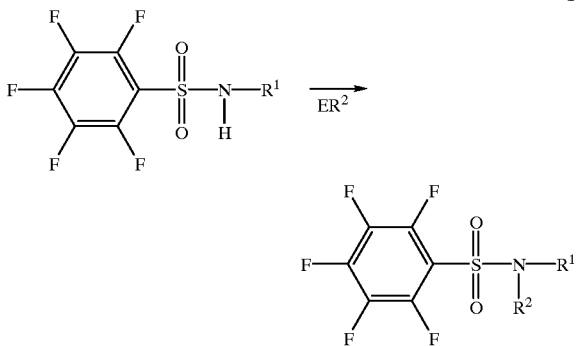

Sulfinic ester

Scheme II
Alternative synthesis of N,N-disubstituted pentafluorophenylsulfonamides

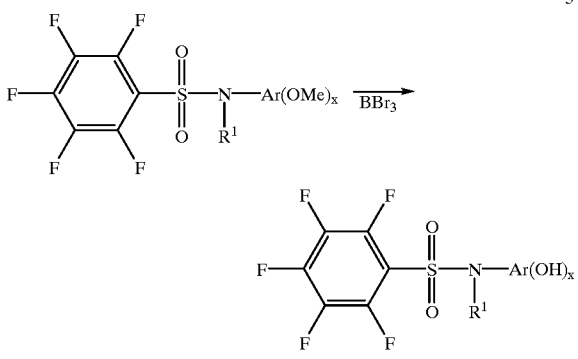

Scheme III
Syntheses of phenols x = 1–3

The invention provides methods of making the subject compounds and compositions. In one general embodiment, the methods involve combining pentafluorophenylsulfonyl chloride with an amine having the general formula $R^1R^2NH$ under conditions whereby the pentafluorophenylsulfonyl chloride and amine react to form the desired compound, and isolating the compound.

Compounds with the generic structure 1 or 3 (Scheme I) may be prepared by reacting the appropriate staring amine in a solvent such as tetaahydrofiuran (TBE), dimethylformamide (DMF), ether, toluene or benzene in the presence of a base such as pyridine, pdimethylaminopyridine, triethylamine, sodium carbonate or potassium carbonate and pentafluorophenylsulfonyl chloride or pentafluorophenylsulfinyl chloride, respectively. Pyridine itself may also be used as the solvent. Preferred solvents are pyridine and DMF and preferred bases are pyridine, triethylamine, and potassium carbonate. This reaction can be carried out at a temperature range of 0° C. to 100° C., conveniently at ambient temperature.

Compounds of the generic structure I can also be obtained by treating the starting sulfonamide (Scheme II) with a base such as LDA, NaH, dimsyl salt, alkyl lithium, potassium carbonate, under an inert atmosphere such as argon or nitrogen, in a solvent such as benzene, toluene, DMF or THF with an allglating group containing a leaving group such a Cl, Br, I, MsO—, TsO—, TFAO—, represented by E in Scheme II. A preferred solvent for this. reaction is THF and the preferred base is lithium bis(trimethylsilyl)amide. This reaction can be carried out at a temperature range of 0° C. to 100° C., conveniently at ambient temperature.

Sulfonic esters (2) and sulfinic esters (4) may be prepared by reacting the appropriate starting phenol in a solvent such as THF, DMF, toluene or benzene in the presence of a base such as pyridine, triethylamine, sodium carbonate, potassium carbonate or 4-dimethylaminopyridine with pentafluorophenylsulfonyl chloride or pentafluorophenylsulfmyl chloride, respectively. Pyridine itself may also be used as the solvent. Preferred solvents are pyridine and DMF and preferred bases are sodium carbonate and potassium carbonate. This reaction can be carried out at a temperature range of 0° C. to 100° C., conveniently at ambient temperature.

Compounds of the general structure 5, in which Ar is an aromatic group and x is from one to three, can be obtained from the corresponding methyl ethers (Scheme III) by reaction with boron tribromide in a solvent of low polarity such as hexanes or $CH_2Cl_2$ under an inert atmosphere at a temperature ranging from −45° to 30° C. In a preferred embodiment, the reaction is carried out in $CH_2Cl_2$ at about 30° C.

Occasionally, the substrates for the transformations shown in Schemes I–III may contain functional groups (for example, amino, hydroxy or carboxy) which are not immediately compatible with the conditions of the given reaction. In such eases, these groups may be protected with a suitable protective group, and this protective group removed subsequent to the transformation to give the original functionality using well know procedures such as those illustrated in T. W. Greene and P. G. M. Wuts, Protective Groups in Organic Synthesis, Second Edition, John Wiley & Sons, Inc., 1991.

The compounds used as initial starting materials in this invention may be purchased from commercial sources or alternatively are readily synthesized by standard procedures which are well know to those of ordinary skill in the art.

Some of the compounds of formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of formula I which are acidic or basic in nature can form a wide variety of salts with various inorganic and organic bases or acids, respectively. These salts must be pharmacologically acceptable for administration to mammals. Salts of the acidic compounds of this invention are readily prepared by treating the acid compound with an appropriate molar quantity of the chosen inorganic or organic base in an aqueous or suitable organic solvent and then evaporating the solvent to obtain the salt. Acid addition salts of the basic compounds of this invention can be obtained similarly by treatment with the desired inorganic or organic acid and subsequent solvent evaporation and isolation.

The compounds of the invention may be labeled in a variety of ways. For example, the compounds may be provided as radioactive isotopes; for example, tritium and the $^{14}C$-isotopes. Similarly, the compounds may be advantageously joined, covalently or noncovalently, to a wide variety of joined compounds which may provide pro drugs or function as carriers, labels, adjuvents, coactivators, stabilizers, etc. Hence, compounds having the requisite structural limitations encompass such compounds joined directly or indirectly (e.g. through a linker molecule), to such joined compounds.

ANALYSIS

The subject compositions were demonstrated to have pharmacological activity in in vitro and in vivo assays, e.g. are capable of specifically modulating a cellular physiology to reduce an associated pathology or provide or enhance a prophylaxis. Preferred compounds are capable of specifically regulating LDL receptor gene expression. Compounds may be evaluated in vitro for their ability to increase LDL receptor expression using western-blot analysis, for example, as described in Tam et al. (1991) J. Biol. Chem. 266, 16764. Established animal models to evaluate hypocholesterolemic effects of compounds are known in the art. For example, compounds disclosed herein are shown to lower cholesterol levels in hamsters fed a high-cholesterol diet, using a protocol similar to that described in Spady et al. (1988) J. Clin. Invest. 81, 300; Evans et al. (1994) J. Lipid Res. 35, 1634; Lin et al (1995) J. Med. Chem. 38, 277.

FORMULATION AND ADMINISTRATION

The invention provides methods of using the subject compounds and compositions to treat disease or provide medicinal prophylaxis, to upregulate LDL receptor gene expression in a cell, to reduce blood cholesterol concentration in a host, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid. semi-solid or liquid media including water and non-toxic organic solvents.

In another embodiment, the invention provides the subject compounds in the form of a pro-drug, which can be metabolically converted to the subject compound by the recipient host. A wide variety of produg formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers, For example, dosage units may be included in a variety of containers including capsules, pills, etc.

The compositions may be advantageously combined and/or used in combination with other hypocholesterolemic and/or hypolipemic therapeutic or prophylactic agents, different from the subject compounds. In many instances, administration in conjunction with the subject compositions enhances the efficacy of such agents. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligan displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $_1$H NMR spectra were recorded on a Varian Gemini 400 MHz NMR spectrometer. Significant peaks are tabulated in the order. multiplicity (s, singlet; d, doublet; t, triplet; q, quartet; m, multiplet), coupling constant(s) in Hertz, number of protons. Electron Ionization (EI) mass spectra were recorded on a Hewlett Packard 5989A mass spectrometer. Fast Atom Bombardment (FAB) mass spectroscopy was carried out in a VG analytical ZAB 2-SE high field mass spectrometer. Mass spectroscopy results are reported as the ratio of mass over charge, and the relative abundance of the ion is reported in parentheses.

Example 1

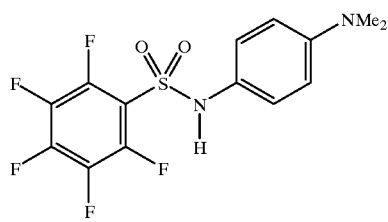

4-(N,N-Dimethylamino)-1-pentafluorophenylsulfonamidobenzene.

To N,N-dimethyl-1,4-phenyldiamine dihydrochloride (3 g, 14.6 mmol) suspended in pyridine (50 mL) at 0° C. under argon was added dropwise pentafluorophenylsulfonyl chloride (2.38 mL, 16 mmol). The reaction mixture was stirred for 30 min at 0° C. and allowed to warm to ambient temperature. The reaction mixwre was stired at room temperature for 3 h. The volume of the mixture was then reduced to 10 mL under reduced pressure. The mixure was diluted with ethyl acetate and the reaction quenched with water. The layers were separated and the aqueous layer extracted twice with ethyl acetate. The organic layers were combined and washed with brine and dried with $MgSO_4$. The solvent was evaporated and the residue purified by chromatography on silica, eluting with $CH_2Cl_2$. The title product was obtained as a white solid in 63% yield (3.4 g). $^1$H NMR ($CDCl_3$): 7.01(d, J=8.9 Hz, 2H), 6.77(s, 1H), 6.59(d, J=8.3 Hz, 2H), 2.92 ppm(s, 6H). FAB m/z (relative abundance): 367(100%, M+H$^+$), 135(30%), 121(25%). Anal. calcd. for $C_{14}H_{11}F_5N_2O_2S$: C, 45.95, H, 3.03, N, 7.65. Found C, 45.83, H, 2.99, N, 7.62

Example 2

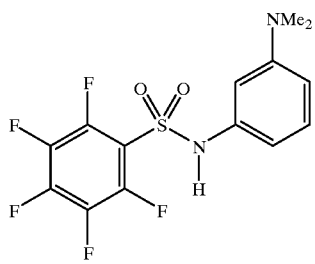

3-(N,N-Dimethylamino)-1-pentafluorophenylsulfonamidobenzene.

$_1$H NMR ($CDCl_3$): 7.12(t, J=8 Hz, 1H), 7.05(s, 1H), 6.57(s, 1H) 6.53(d, J=8 Hz, 1H), 6.40(d, J=8 Hz, 1H), 2.94 ppm (s, 6H). FAB m/z: 366(100%, M$^+$). The compound was prepared by a protocol similar to that of example 1 by replacing N,N-dimethyl-1,4-phenyldiamine dihydrochloride with 3-(N,N-dimethylamino)aniline.

Example 3

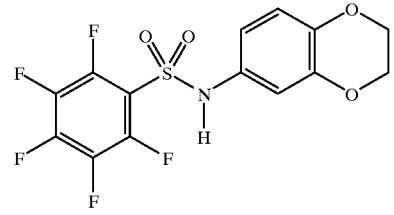

1,2-Ethylenedioxy-4-pentafluorophenylsulfonamidobenzene.

$^1$H NMR ($CDCl_3$): 6.97(s, 1H) 6.76(d, J=8.6 Hz, 1H), 6.72(d, J=2.6 Hz, 1H), 6.62(dd, J=8.6, 2.6 Hz, 1H), 4.21 ppm (s, 4H). FAB m/z: 381(100%, M+H$^+$). Anal calcd. for $C_{14}H_8F_5NO_4S$: C, 44.09, H, 2.12, N, 3.68, S, 8.39. Found: C, 43.83, H, 2.19, N, 3.62, S, 8.20. The compound was prepared by a protocol similar to that of example 1 by replacing N,N-dimethyl-1,4-phenyldiamine dihydrochloride with 3,4-ethylenedioxyaniline.

Example 4

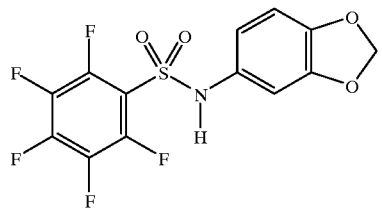

1,2-Methylenedioxy-4-pentafluorophenylsulfonamidobenzene.

$^1$H NMR ($CDCl_3$): 6.85(s, 1H), 6.78(s, 1H), 6.70(d, J=8 Hz, 1H), 6.57(d, J=8 Hz, 1H), 5.97 ppm(s, 2H). The compound was prepared by a protocol similar to that of example 1 by replacing N,N-dimethyl-1,4-phenyldiamine dihydrochloride with 3,4-methylenedioxyaniline.

Example 5

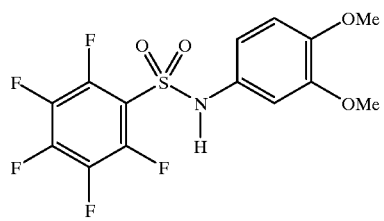

1,2-Dimethoxy-4-pentafluorophenylsulfonamidobenzene.

$^1$H NMR ($CDCl_3$): 6.98(s, 1H), 6.85(d, 1H), 6.74(d, 1H), 6.60(dd, 1H), 3.85(s, 3H), 3.83 ppm (s, 3H). EI, m/z: 383(50, M$^+$), 152(100). The compound was prepared by a protocol similar to that of example 1 by replacing N,N-dimethyl-1,4-phenyldiamine dihydrochloride with 3,4-dimethoxyaniline.

Example 6

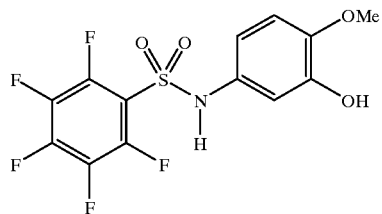

2-Hydroxy-1-methoxy-4-pentafluorophenylsulfonamidobenzene. $^1$H NMR (CDCl$_3$): 6.93(s, 1H), 6.7–6.8(m, 3H), 5.68(bs, 1H), 3.85 ppm(s, 3H). EI, m/z: 333(20, M$^+$), 138(100). mp 118–120° C. The compound was prepared by a protocol similar to that of example 1 by replacing N,N-dimethyl-1,4-phenyldiamine dihydrochloride with 3-hydroxy-4-methoxyaniline.

Example 7

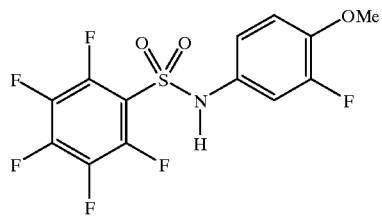

2-Fluoro-1-methoxy 4-pentafluorosulfonamidobenzene. $^1$H NMR (DMSO) 11.15(broad s, 1H), 7.13(t, J=9 Hz, 1H), 7.02(dd, J=9.5 2.5 Hz, 1H), 6.94 ppm (dd, J=8.8 1.5 Hz, 1H), 3.79 ppm (s, 3H). EI, m/z: 371(20, M$^+$), 140(100). Anal. calcd. for C$_{13}$H$_7$HF$_6$N$_1$O$_3$S$_1$: C, 42.06, H, 1.90, N, 3.77, S, 8.64. Found: C, 42.19, H, 1.83, N, 3.70, S, 8.60. Mp 118–119° C. The compound was prepared by a protocol similar to that of example 1 by replacing N,N-dimethyl-1,4-phenyldiamine dihydrochloride with 3-fluoro-p-anisidine.

Example 8

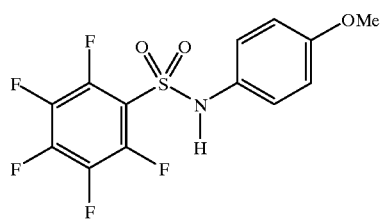

4-Methoxy-1-pentafluorophenylsulfonamidobenzene. $^1$H NMR (CDCl$_3$): 6.99(s, 1H), 6.96(d, J=4 Hz, 2H), 6.88(d, J=4 Hz, 2H), 3.83 ppm(s, 3H). EI, m/z: 353(60, M$^+$), 122(100). M.p. 102–103° C. The compound was prepared by a protocol similar to that of example 1 by replacing N,N-dimethyl-1,4-phenyldiamine dihydrochloride with 4-methoxyaniline.

Example 9

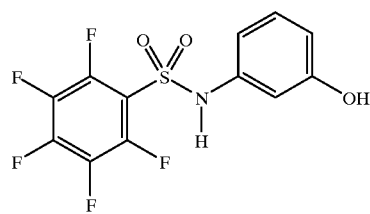

3-Hydroxy-1-pentafluorophenylsulfonamidobenzene. $^1$H NMR (CD$_3$OD): 7.15(t, J=8.1 Hz, 1H), 6.67(t, J=2.2 Hz, 1H) 6.60(dd, J=1.3 Hz, 7.8 Hz, 1H), 6.52 ppm (dd, J=2.4 Hz 8.3 Hz, 1H). EI, m/z: 339(80, M$^+$), 256(50), 81(100). The compound was prepared by a protocol similar to that of example 1 by replacing N,N-dimethyl-1,4-phenyldiamine dihydrochloride with 3-hydroxyaniline.

Example 10

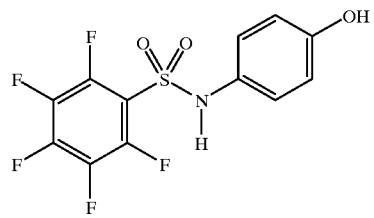

4-Hydroxy-1-pentafluorosulfonamidobenzene. $^1$H NMR (CD$_3$OD): 6.95(d, J=8.9 Hz, 2H), 6.65 ppm (d, J=8.9 Hz, 2H). EI, m/z: 339(30, M$^+$). The compound was prepared by a protocol similar to that of example 1 by replacing N,N-dimethyl-1,4-phenyldiamine dihydrochloride with 4-hydroxyaniline.

Example 11

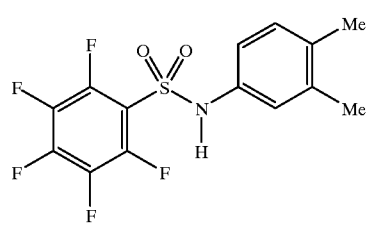

1,2-Dimethyl-4-pentafluorophenylsulfonamidobenene. $^1$H NMR (CDCl$_3$): 7.03(d, J=7.9 Hz, 1H), 6.92(s, 1H), 6.85–6.82(m, 2H), 2.18(s, 3H), 2.16 ppm(s, 3H). The compound was prepared by a protocol similar to that of example 1 by replacing N,N-dimethyl-1,4-phenyldiamine dihydrochloride with 3,4-dimethylaniline.

Example 12

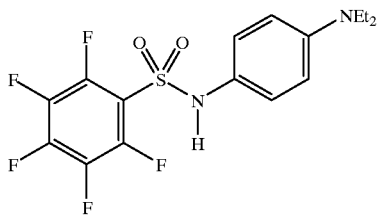

4(N,N-Diethylamino)-1-pentafluorophenylsulfonamidobenzene. $^1$H NMR (CDCl$_3$): 6.93(d, J=8.8 Hz, 2H), 6.78(s, 1), 6.45(d, J=8.7 Hz, 2H), 3.25(dd, J=7.0 Hz, 7.3 Hz,4H), 1.10 ppm(t, J=7.2 Hz, 6H). The compound was prepared by a protocol similar to that of example 1 by replacing N,N-diethyl-1,4-phenyldiamine dihydrochloride with 4-(N,N-diethylamino)aniline.

Example 13

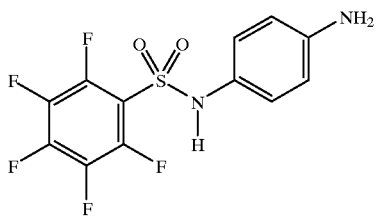

4Amino-1-pentafluorophenylsulfonamidobenzene. $^1$H NMR (CDCl$_3$): 6.82(d, J=8.7 Hz, 2H), 6.49 ppm(d, J=8.7 Hz, 2H). EI, m/z: 338(7, M$^+$), 107(100), 80(40). The compound was prepared by a protocol similar to that of example 1 by replacing N,N-dimethyl-1,4-phenyldiamine dihydrochloride with 1,4-diaminobenzene.

Example 14

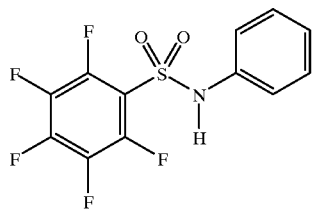

Pentafluorophenylsulfonamidobenzene. $^1$H NMR (CDCl$_3$): 7.30(d, J=8 Hz, 2H), 7.13–7.2(m, 3H), 7.0 ppm(s, 1H). EI, m/z: 323(90, M$^+$), 92(100). The compound was prepared by a protocol similar to that of example 1 by replacing N,N-dimethyl-1,4-phenyldiamine dihydrochloride with aniline.

Example 15

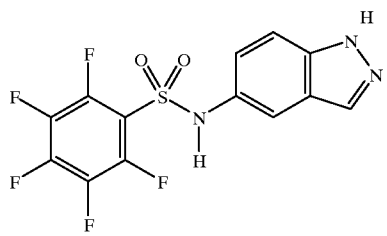

5-Pentafluorophenylsulfonamidoindazole. $^1$H NMR (CD$_3$OD): 7.98(s, 1H), 7.69(s, 1H), 7.47(d, J=8.3 Hz, 1H), 7.23 ppm(d, J=8.3 Hz, 1H). EI m/z: 364(50, M+H$^+$), 133 (100). The compound was prepared by a protocol similar to that of example 1 by replacing N,N-dimethyl-1,4-phenyldiamine dihydrochloride with 5-aminoindazole.

Example 16

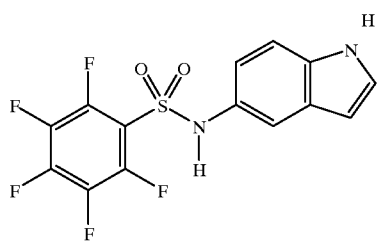

5-Pentafluorophenylsulfonamidoindole. $^1$H NMR (CDCl$_3$): 8.2(s, 1H), 7.43(s, 1H), 7.3(d, J=8 Hz, 1H), 7.22(s, 1H)), 6.98(d, J=8 Hz, 1H), 6.92 ppm (s, 1H), 6.50 ppm(s, 1H). EI m/z: 362(M$^+$), 131(100). The compound was prepared by a protocol similar to that of example 1 by replacing N,N-dimethyt-1,4-phenyldiamine dihydrochloride with 5-aminoindole.

Example 17

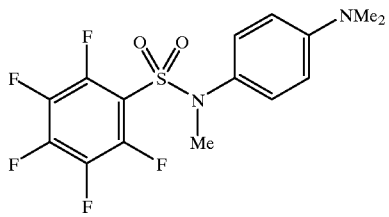

4-(N,N-Dimethylamino)-1-(N-methylpentafluorophenylsulfonamido)benzene.

4-(N,N-Dimethylamino)-1-(pentafluorophenylsulfonamido)benzene (100 mg, 0.273 mmol) was dissolved in dry THF (2.5 mL) and to the system was added under N$_2$ at room temperature a 1M solution of lithium bis(trimethylsilyl)amide (0.274 mL). The reaction mixture was stirred for 10 min followed by addition of MeI (65 mg, 0.028 mL). The reaction mixture was stirred overnight, the solvent was evaporated under reduced pressure and the crude product purified by HPLC using silica as the stationary phase and eluting with 20%EtOAc/Hex (v/v) to afford the product as a white solid in 60% yield (62 mg). EI m/z: 380(35, M$^+$), 149(100). $^1$H NMR (CD$_3$OD) 7.05(d, J=8 Hz, 2H), 6.68(d, J=8 Hz, 2H), 3.33(s, 3H) 2.93(s, 6H). Anal. calcd. for $C_{15}H_{13}F_5SO_2N_2$: C, 47.37, H, 3.45, N, 7.37. Found: C, 47.37, H, 3.49, N, 7.32.

Example 18

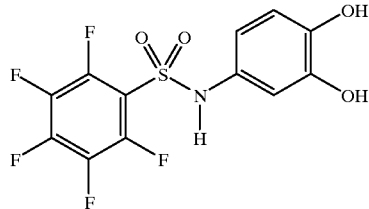

1,2-Dihydroxy-4-pentafluorophenylsulfonamidobenzene. 1-Hydroxy-2-methoxy-4-pentafluorophenylsulfonamidobenzene (250 mg, 0.678 mmol) was suspended in dry $CH_2Cl_2$ (5 mL) at 0° C. under nitrogen. To the mixture was added $BBr_3$ as a 1M solution in $CH_2Cl_2$ (0.746 mmol, 1.1 eq.). The mixture was warmed to ambient temperature and stirred overnight. The reaction mixture was poured over ice (75 mL) and extracted 3 times with 30 mL portions of $CH_2Cl_2$. The organic layer was dried with $MgSO_4$ and the solvent was evaporated. The crude product was purified by chromatography over silica eluting with 30% (v/v) EtOAc/Hex to afford the product as a white solid in 41% yield (98 mg). $^1$H NMR (DMSO): 10.63(s, 1H), 9.15(s, 1H), 8.91(s, 1H), 6.61(d, J=9 Hz, 1H), 6.58(d, J=3 Hz, 1H), 6.39 ppm(dd, J=9 Hz 3 Hz, 1H).

Example 19

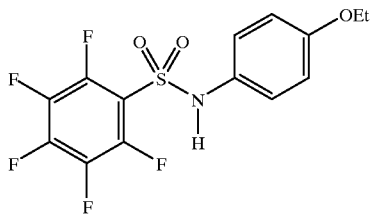

4-Ethoxy-1-pentafluorophenylsulfonamidobenzne. To a strred solution of p-phenetidine (0.100 g, 0.729 mmol) in dimnethylformamide (3.65 mL) at 25° C. was added pentafluorophenyl sulfonyl chloride (0.135 mL, 0.911 mmol), followed by sodium carbonate (0.116 g, 1.09 mmol), and the reaction mixture was stirred for 18 hours. Ihe reaction mixture was diluted with ethyl acetate (50 mL) and washed with 20% ammonium chloride (2×20 mL) and saturated sodium chloride (2×20 mL). The organic layer was dried (sodium sulfite), and the ethyl acetate was removed under reduced pressure to yield a reddish-brown oil. Column chromatography (3:1 ethyl acetate/hexane) yielded the title compound (0.222 g, 83%). $^1$H NMR ($CDCl_3$) 7.08(d, J=9 Hz, 2H, 7.04(s, 1H), 6.80(d, J=9 Hz, 2H), 3.96(q, J=7 Hz, 2H), 1.37 ppm (t, J=7 Hz, 2H). IR (neat) 3000–3600, 1750 cm$^{-1}$. EI m/z: 367(M$^+$), 154, 136.

The compounds of Examples 20 through 26 were prepared by a protocol similar to that of Example 19 by replacing p-phenetidine with the appropriate amine.

Example 20

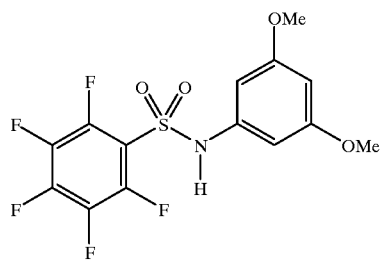

3,5-Dimethoxy-1-pentafluorophenylsulfonamidobenzene. The compound was prepared by to a protocol similar to that of Example 19 by replacing p-phenetidine with 3,5-dimethoxyanine. $^1$H NMR ($CDCl_3$) 6.91(s, 1H), 6.32(s, 2H), 6.25(s, 1H), 3.72 ppm(s, 6H).

Example 21

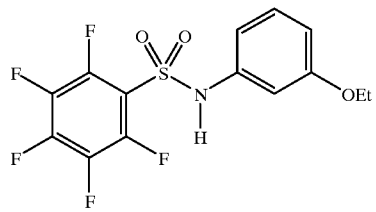

3-Ethoxy-1-pentafluorophenylsulfonamidobenzene The compound was prepared by a protocol slimilar to that of Example 19 by replacing p-phenetidine with 3-ethoxyaniline. $^1$H NMR ($CDCl_3$) 7.35(t, J=8 Hz, 1H), 7.21(s, 1H), 6.92(s, 1H), 6.86(d, J=8 Hz,1H), 6.83(d, J=8 Hz, 1H), 4.15(q, J=6 Hz, 2H, 1.56 ppm (t, J=6 Hz, 3H).

Example 22

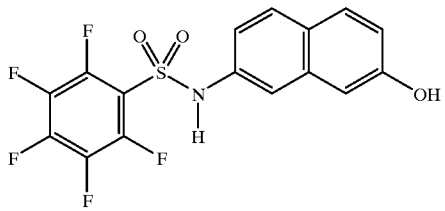

7-Hydroxy-2-pentafluorophenylsulfonamidonaphthalene. The compound was prepared by a protocol similar to that of Example 19 by replacing p-phenetidine with 2-amino-7-hydroxynaphthalene. $^1$H NMR ($CDCl_3$) 8.15(t, J=8 Hz, 1H), 7.55(d, J=8 Hz, 1H), 7.44(s, 1H), 7.42(d, J=8 Hz, 1H), 7.40(s, 1H), 6.88 ppm (q, J=8 Hz, 1H).

Example 23

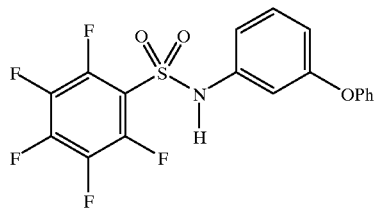

3-Phenoxy-1-pentafluorophenylsulfonamidobenzene. The compound was prepared by a protocol similar to that of Example 19 by replacing p-phenetidine with 3-phenoxyaniline. $^1$H NMR (CDCl$_3$) 7.34(t, J=8 Hz, 2H), 7.26(t, J=8 Hz, 1H), 7.16(t, J8 Hz, 1H), 6.94(d, J=8 Hz, 2H), 6.86(d, J=8 Hz, 1H), 6.82(d, J=8 Hz, 1H), 6.74(s, 1H).

Example 24

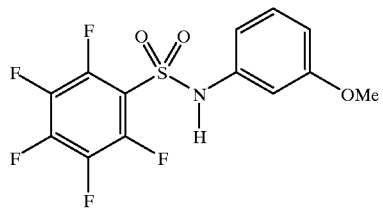

3-Methoxy-1-pentafluorophenylsulfonamidobenzene. The compound was prepared by a protocol similar to that of Example 19 by replacing p-phenetidine with 3-methoxyaniline. $^1$H NMR (CDCl$_3$) 7.20(d, J=8 Hz 1H, ), 6.95(s, 1H), 6.78(d, J=8 Hz 1H,), 6.70(t, J=8 Hz, 1H), 3.79 ppm (s, 1H).

Example 25

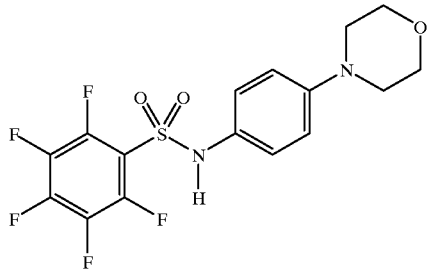

4-(1-Morpholino)-1-pentafluorophenylsulfonamidobenzene. The compound was prepared by a protocol similar to that of Example 19 by replacing p-phenetidine with 4(1-morpholino)aniline. $^1$H NMR (CDCl$_3$) 7.09(d, J=8 Hz, 2H), 6.85(d, J=8 Hz, 2H), 3.85(t, J=8 Hz, 4H), 3.15 ppm (t, J=8 Hz, 4H).

Example 26

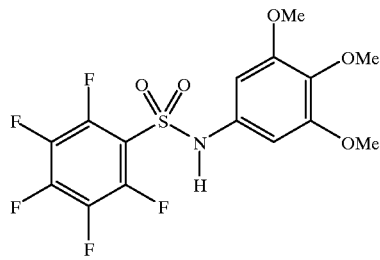

5-Pentafluorophenylsulfonamido-1,2,3-trimethoxybenzene. The compound was prepared by a protocol similar to that of Example 19 by replacing p-phenetidine with 3,4,5-trimethoxyaniline. $^1$H MNR (CDCl$_3$) 8.14(s, 1H), 6.46(s, 2H), 3.69(s, 6H), 3.59(s, 3H).

Example 27

1,3-Dimethoxy-2-hydroxy-5-pentafluorophenylsulfonamidobenzene. 1,2-Dihydroxy-3-methoxy-5-pentafluorophenylsulfonamidobenzene. 5-Pentafluorophenylsulfonamido-1,2,3-trihydroxybenzene. 1,2,3-Methoxy-5-pentafluorophenylsulfonamidobenzene (269 mg, 0.6 mmol) was suspended in dry CH$_2$Cl$_2$ (5 mL) at 0° C. under nitrogen. To the mixture was added BBr$_3$ as a 1M solution in CH$_2$Cl$_2$ (3.26 mmol, 5 eq.). The mixture was warmed to ambient temperature and stirred overnight The reaction mixture was poured over ice (75 mL) and extted 3 times with 30 mL portions of CH$_2$Cl$_2$. The organic layer was dried with MgSO$_4$, evaporated, and the residue was subjected to chromatography over silica eluting with 30% (v/v) EtOAc/Hex to afford the three products. The compounds of Examples 28 and 29 were prepared in a manner similar to that described above beginning with the product of Example 20 and treating it with BBr$_3$.

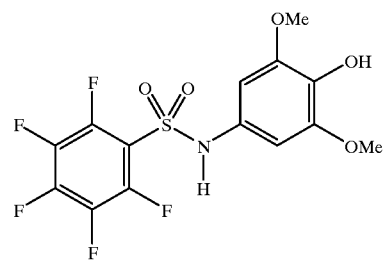

1,3-Dimethoxy-2-hydroxy-5-pentafluorophenylsulfonamidobenzene. $^1$H NMR (CDCl$_3$) 10.85(s, 1H), 8.31(s, 1H), 6.41(s, 2H), 3.66 ppm (s, 6H).

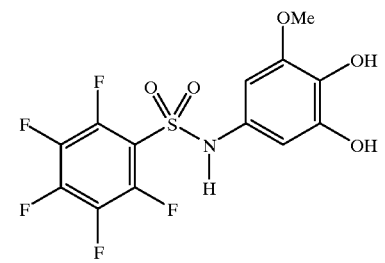

1,2-Dihydroxy-3-methoxy-5-pentafluorophenylsulfonamidobenzene. $^1$H NMR (CDCl$_3$)

10.73(s, 1H), 8.31(s, 1H), 6.27(s, 1H), 6.26(s, 1H), 3.66 ppm (s, 3H).

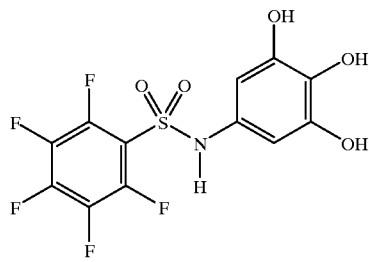

5-Pentafluorophenylsulfonamido-1,2,3-trihydroxybenzene. $^1$H NMR (CDCl$_3$) 11.0(s, $^1$H), 9.03(s, 2H), 8.06(s, 1H), 6.13 ppm (s, 2H).

Example 28

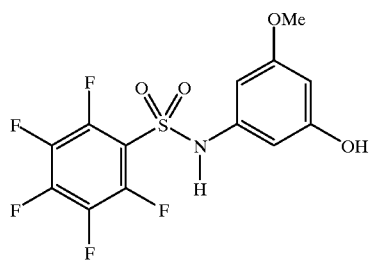

3-Hydroxy-5-methoxy-1-pentafluorophenylsulfonamidobenzene. $^1$H NMR (CDCl$_3$) 11.2(s, 1H), 9.63(s, 1H), 6.23(s, 1H), 6.21(s, 1H, 6.08(s, 1H), 3.63(s, 3H).

Example 29

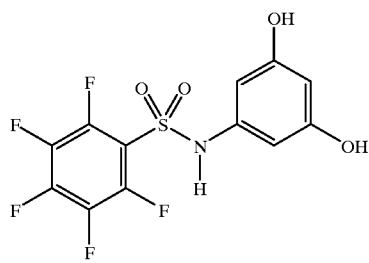

3,5-Dihydroxy-1-pentafluorophenylsulfonamidobenzene. $^1$H NMR (CDCl$_3$) 7.15(s. 1H), 6.25(s, 2H), 6.15(s, 1H), 5.31(s, 2H).

Example 30

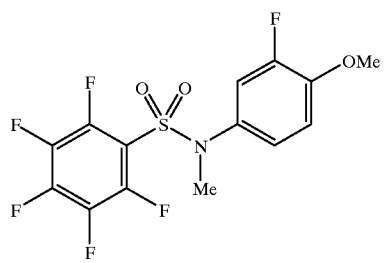

2-Fluoro-1-methoxy-4-(N-methylpentafluorophenylsulfonamido)benzene. Prepared using a procedure similar to that of Example 18 replacing 4-(N,N-dimethylamino)-1-pentafluorophenylsulfonamidobenzene with the appropriate non-substituted sulfonamide (product of Example 7). $^1$H NMR (CDCl$_3$): 6.97–6.94(m, 2H), 6.89(t, J=9 Hz, 1H), 3.87(s, 3H), 3.35 ppm (t, J=1 Hz). EI m/z: 385(20, M$^+$), 154(100). Anal. calcd. for C$_{14}$H$_9$F$_6$NO$_3$: C, 43.64, H, 2.35, N, 3.64. Found C, 43.55, H, 2.38, N, 3.65.

Example 31

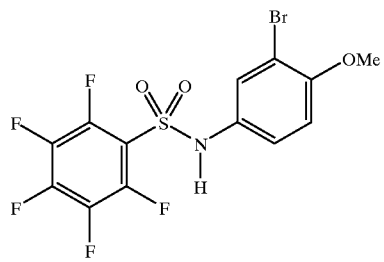

2-Bromo-1-methoxy-4-pentafluorophenylsulfonamidobenzene. $^1$H NMR (CDCl$_3$): 7.3 5(d, J=3 Hz, 1H), 7.15(dd, J=9 Hz, 3 Hz, 1H), 6.97(s, 1H), 6.81(d, J=9 Hz, 1H), 3,88 ppm (s, 3H). EI m/z: 433(35, M$^+$), 202(100). The compound was prepared by a protocol similar to that of example 1 by replacing N,N-dimethyl-1,4-phenyldiamine dihydrochloride with 3-bromo-4-methoxyaniline.

Example 32

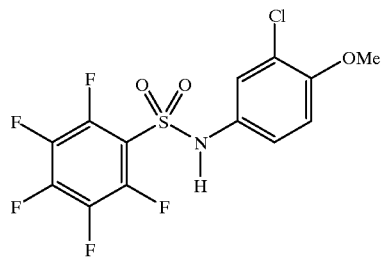

2-Chloro-1-methoxy-4-pentafluorophenylsulfonamidobenzene. $^1$H NMR (CDCl$_3$): 7.19(d, J=3 Hz, 1H), 7.08(dd, J=9 Hz, 3 Hz, 1H), 7.01(s, 1H), 6.84(d, J=9 Hz, 3.85(s, 3H). EI m/z(rel. abundance): 387(10, M$^+$), 156(100). The compound was prepared by a protocol similar to that of example 1 by replacing N,N- dimethyl-1,4-phenyldiamine dihydrochloride with 3-chloro-4-methoxyaniline.

Example 33

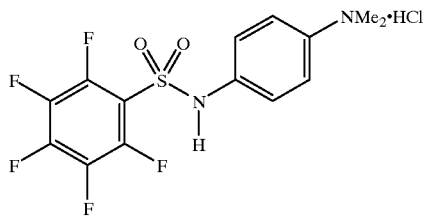

4N,N-Dimethylamino)-1-pentafluorophenylsulfonamidobenzene hydrochloride. 4-(N,N-Dimethylamino)-1-pentafluorophenylsulfonamidobenzene (2 g, 5.5 mmol) was dissolved in 15 mL of diethyl ether at ambient temperure under nitrogen. Gaseous HCl wa bubbled into the reaction mixture for 5 min The mixture was filtered and the resulting solid washed twice with 15 mL portions of ice cold diethyl ether to afford the product as a white solid (1.89 g, 86% yield). $^1$H NMR (CD$_3$OD): 7.62(dd, J=9.0 Hz, 1.6 Hz, 2H), 7.44(dd, J=9.0 Hz, 1.6 Hz, 2H), 3.28 ppm(s, 6H). FAB m/z: 367(100%, M+H$^+$), 135(90%), 121(45%). Anal. calcd. for C$_{14}$H$_{13}$ClF$_5$N$_2$O$_2$S: C, 41.79, H, 3.01, N, 6.97, S, 7.95. Found C, 41.71, H, 3.05, N, 7.01, S, 7.96.

Example 34

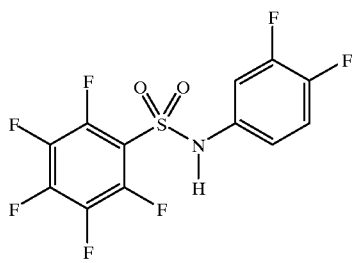

3,4-Difluoro-1-pentafluorophenylsulfonamidobenzene. The compound was prepared in a manner similar to that of example 1 by replacing N,N-dimethyl-1,4-phenyldiamine dihydrochloride with 3,4-difluoroaniline. $^1$H NMR (CDCl$_3$) 7.13(m, 3H), 6.91 ppm (m, 1H). EI, m/z (relative abundance): 359(20), 128(100). Anal. calcd. for C13H4F7N1O2S1: C, 40.12, H, 1.12, N, 3.90. Found: C, 40.23, H, 1.17, N, 3.89.

Example 35

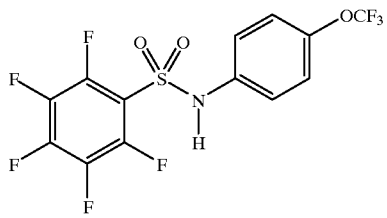

4-Trifluoromethoxy-1-pentafluorophenylsulfonamidobenzene. The compound was prepare in a manner similar to that of example 1 by replacing N,N-dimethy-1,4-phenyidiamine dihydrochloride with 4-(trifluoromethoxy)aniline. $^1$H NMR (CDCl$_3$) 7.18 ppm (m, 4H). EI, m/z(relative abundance):407(20), 176(100). Anal. calcd. for C13H5F8N1O3S1: C, 38.34, H, 1.24, N, 3.44. Found: C, 38.33, H, 1.30, N, 3.43.

Example 36

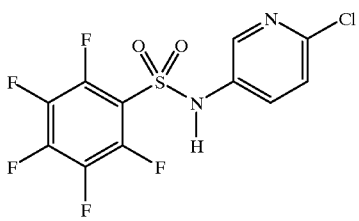

2-Chloro-5-pentafluorophenylsulfonamdopyridine. The compound was prepared in a manner similar to that of example 1 by replacing N,N-dimethyl-1,4-phenyldiamine dihydrochloride with 5-amino-2-chloropyridine. H NMR (DMSO-d$^6$): 8.18(d, J=2.68 Hz, 1H), 7.64(dd, J=8.75, 2.89 Hz, 1H), 7.50 ppm (d, J=8.75 Hz, 1H). EI m/z 358(20, M$^+$), 127(100). Anal. calcd. for C$_{11}$H$_4$ClF$_5$N$_2$O$_2$S: C, 36.83, H, 1.12, N, 7.81, S, 8.94, Cl 9.90. Found: C, 37.00, H, 1.16, N, 7.78, S, 8.98, Cl 10.01. White crystals with M.P.=144–145° C.

Example 37

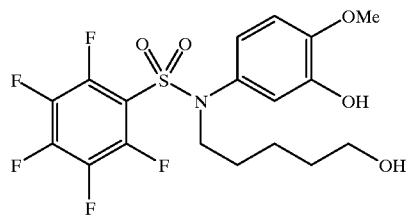

2-Hydroxy-1-methoxy-4-(N-(5-hydroxypentyl)-pentafluorophenylsulfonamido)benzene. N-(5-hydroxypentyl)-2-hydroxy-1-methoxy-4-aminobenzene was prepared by reductive amination of 5-amino-2-methoxy phenol with glutaric dialdehyde with NaBH$_4$ in MeOH. 2-Hydroxy-1-methoxy-4-(N-(5-hydroxypentyl)-pentafluorophenylsulfonamido)benzene was prepared in a manner similar to that of example 1 by replacing N,N-dimethyl-1,4-phenyldiamine dihydrochloride with N-(5-hydroxypentyl)-2-hydroxy-1-methoxy-4-aminobenzene. $^1$H NMR (CDCl$_3$): 6.78(d, J=8.6 Hz, 1H), 6.71(dd, J=8.59, 2.48 Hz, 1H), 6.63(d, J=2.48 Hz, 1H), 3.88(s, 3H), 3.7(t, J=6.8 Hz, 2H), 3.6(t, J=6.39 Hz, 2H), 1.5 ppm (m, 6H). Anal. calcd. for C$_{18}$H$_{18}$F$_5$NO$_5$S: C, 47.47, H, 3.98, N, 3.08, S, 7.04. Found: C, 47.47, H, 4.04, N, 3.11, S, 6.97. White crystals with M.P.=118°.

Example 38

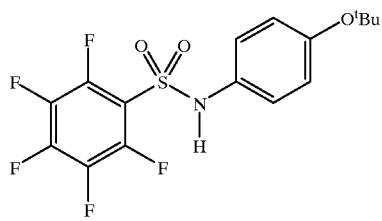

4-(1,1-Dimethyl)ethoxy-1-pentafluorophenylsulfonamidobenzene. The compouid was prepared in a manmer similar to example 46 by replacing 3-chloroaniline with 4-t-butoxyanilime. 4-t-Butoxyaniline was prepared by thie method of Day (*J. Med. Chem.* 1975, 18, 1065). $^1$H NMR (CDCl$_3$): d 7.07(m, 2), 6.92(m, 2), 6.88(m, 1), 1.31(s, 9). MS (EI): m/z 395(1, M$^+$), 339(28), 108(100). Anal. Calcd. for C$_{16}$H$_{14}$F$_5$NO$_3$S: C, 48.61; H, 3.57; N, 3.54; S, 8.11. Found: C, 48.53; H, 3.60; N, 3.50; S, 8.02.

Example 39

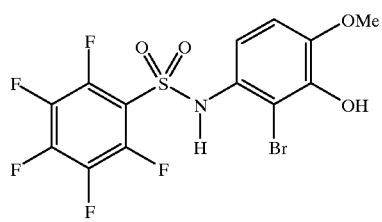

1-Bromo-3-hydroxy-4-methoxy-1-pentafluorophenylsulfonamidobenzene. The compound was prepared by bromination of the compound of example 6 with N-bromosuccmimide in dichloromedtane. $^1$H NMR (CDCl$_3$) 7.28(br s, 1H), 7.21(d, J=9 Hz, 1H), 6.80(d, J=9 Hz, 1H), 6.05(s, 1H), 3.89 ppm (s, 3H). EI, m/z (relative abundance): 449(25), 447(25), 218(100), 216(100). Anal. calcd. for C13H8Br1F5N1O4S1: C, 34.84, H, 1.57, N, 3.13, S, 7.15. Found: C, 34.75, H, 1.60, N, 3.07, S, 7.08.

Example 40

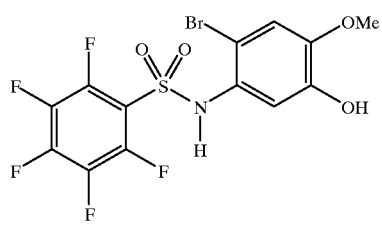

2-Bromo-4-methoxy-5-hydroxy-1-pentafluorophenylsulfonamidobenzene. The compound was prepared by bromination of the compound of example 6 with N-bromosuccinimide in dichloromethane. $^1$H NMR (CDCl$_3$) 7.28(s, 1H), 7.16(br s, 1H), 6.91(s, 1H), 5.63(s, 1H), 3.85 ppm (s, 3H). EI, m/z (relative abundance): 449 (25), 447(25), 218(100), 216(100). Anal. calcd. for C13H8Br1F5N1O4S1: C, 34.84, H, 1.57, N, 3.13, S, 7.15. Found: C, 34.84, H, 1.57, N, 3.05, S, 7.06.

Example 41

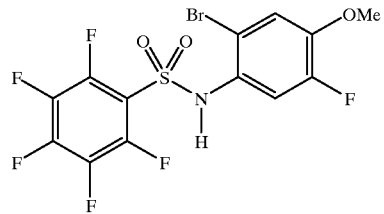

1-Bromo-4-fluoro-5-methoxy-2-pentafluorophenylsulfonamidobenzene. The compound was prepared by bromination of the compound of example 7 with bromine water. $^1$H NMR (CDCl$_3$): 7.49(d, J=11.72 Hz, 1H), 7.21(s, 1H), 7.04(d, J=8.2 Hz, 1H), 3.84 ppm (s, 3H). EI m/z: 449(20, M$^+$), 451(20 ), 228(100), 230(100). Anal. Calcd. for C$_{13}$H$_6$BrF$_6$NO$_3$S: C, 34.69, H, 1.34, N, 3.11, S, 7.12, Br, 17.75. Found: C, 34.76, H, 1.29, N, 3.05, S, 7.12, Br, 17.68. White crystals with M.P.=109° C.

Example 42

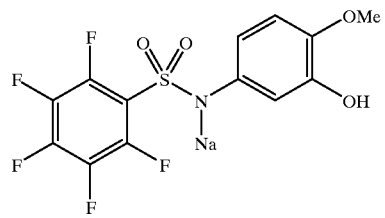

2-Hydroxy-1-methoxyApentafluormphenylslfonamidobenzene sodium salt. The compound was prepared by treating the compound of exmple 6 with an equimolar amount of 1N NaOH$_{(aq)}$. The mixture was then lyophilized and the residue recrystallyzed from ethyl acetate/ether. $^1$H NMR (DMSO) 8.40(s, 1H), 6.57(d, J=9 Hz, 1H), 6.39(d, J=2 Hz, 1H), 6.24(dd, J=9, 2 Hz, 1H), 3.62 ppm (s, 3H). Anal. calcd. for C13H7F5N1Na1O4S1: C, 39.91, H, 1.80, N, 3.58, Na 5.88, S, 8.19. Found: C, 39.79, H, 1.86, N, 3.50, Na 5.78, S, 8.07.

Example 43

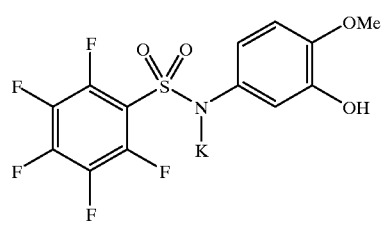

2-Hydroxy-1-methoxy-4-pentafluorophenylsulfonamnidobenzene potassium salt. The compound was prepared in a manner similar to that of example 42 by replacing 1N NaOH with 1N KOH. $^1$H NMR (DMSO) 8.30(br s, 1H), 6.55(d, J=9 Hz, 1H), 6.36(d, J=2 Hz, 1H), 6.25(dd, J=9, 2 Hz, 1H), 3.61 ppm (s, 3H). Anal. calcd. for C13H7F5K1N1O4S1: C, 38.33, H, 1.73, N, 3.44, S, 7.87. Found: C, 38.09, H, 1.79, N, 3.39, S, 7.97.

Example 44

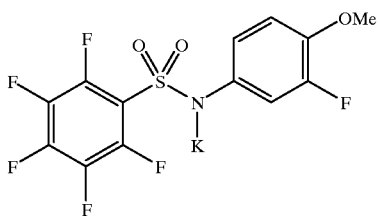

2-Fluoro-1-methoxy-4-pentafluorophenylsulfonamidobenzene potassium salt The compound was prepared in a manner similar to that of example 43 by replacing the compound from example 6 with example 7. $^1$H NMR (DMSO) 6.80(t, J=10 Hz, 1H), 6.72(dd, J=9, 2 Hz, 1H), 6.54(dd, J=9, 2 Hz, 1H), 3.68 ppm (s, 3H). Anal. calcd. for C13H6F6K1N1O3S1: C, 38.15, H, 1.48, N, 3.42, S, 7.83. Found: C, 38.09, H, 1.51, N, 3.35, S, 7.73. M.P.=202–205° C.

Example 45

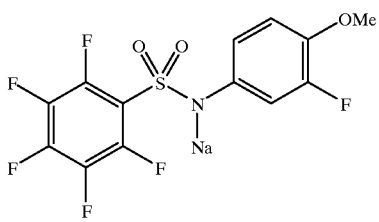

2-Fluoro-1-methoxy-4-pentafluorophenylsulfonamidobenzene sodium salt. The compound was prepared in a manner similar to that of example 44 by replacing 1N KOH with 1N NaOH. $^1$H NMR (DMSO) 6.80(t, J=10 Hz, 1H), 6.71(dd, J=9, 2 Hz, 1H), 6.53(dd, J=9, 2 Hz, 1H), 3.69 ppm (s, 3H). Anal. calcd. for C13H6F6N1Na1O3S1: C, 39.71, H, 1.54, N, 3.56, Na 5.85, S, 8.15. Found: C, 39.56, H, 1.62, N, 3.49, Na 5.88, S, 8.08. M.P. >250° C.

Example 46

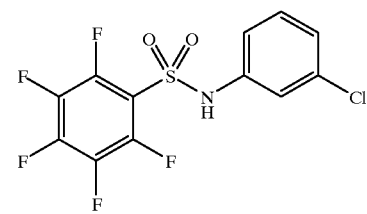

3-Chloro-1-pentafluorophenylsulfonamidobenzene. To a solution of pentafluorophenylsulfonyl chloride (0.15 mL, 1.00 mmol) in MeOH (4 mL) was added 3-chloroaniline (260 mg, 2.04 mmol). After stirring at rt for 1 h, the reaction mixture was concentrated under reduced pressure and the residue was taken up in EtOAc and then filtered through a plug of silica gel. The filtrate was concentrated to give a yellow oil that upon chromatography provided 265 mg (74%) of product. $^1$H NMR (CDCl$_3$): d 7.28–7.24(m, 1H), 7.21–7.17(m, 2H), 7.10–7.08(m, 1H), 7.07(s, 1H). MS (EI): m/z 357(42, M$^+$), 258 (76), 126(87), 99(100). Anal. Calcd. for C$_{12}$H ClF$_5$NO$_2$S: C, 40.30; H, 1.41; N, 3.92; S, 8.96. Found: C, 40.18; H, 1.35; N, 3.84; S, 8.90.

Example 47

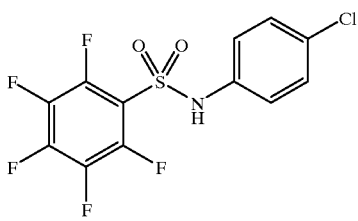

4-Chloro-1-pentafluorophenylsulfonamidobenzene. The compound was prepared in a manner similar to that described in example 46 by replacing 3-chloraniline with 4-chloroaniline. $^1$H NMR (CDCl$_3$): d 7.30(m, 2H), 7.20(m, 1H), 7.14(m, 2H). MS (EI): m/z 357(27, M$^+$), 258(38), 126(100), 99(85). Anal. Calcd. for C$_{12}$H$_5$ClF$_5$NO$_2$S: C, 40.30; H, 1.41; N, 3.92; S, 8.96. Found: C, 40.19; H, 1.37; N, 3.87; S, 8.88.

Example 48

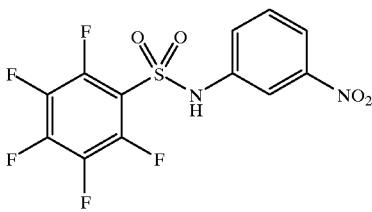

3-Nitro-1-pentafluorophenylsulfonamidobenzene. The compound was prepared in a manner similar to that described in example 46 by replacing 3-chloroanile with 3-nitroaniline. $^1$H NMR (CDCl$_3$): d 8.14(s, 1H), 8.06–8.03 (m, 2H), 7.66–7.63(m, 1H), 7.55(m, 1H). MS (EI): m/z 368(54, M$^+$), 137(70), 91(100). Anal. Calcd. for C$_{12}$H$_5$F$_5$N$_2$O$_4$S: C, 39.14; H, 1.37; N, 7.61; S, 8.71. Found: C, 39.39; H, 1.45; N, 7.46; S, 8.58.

Example 49

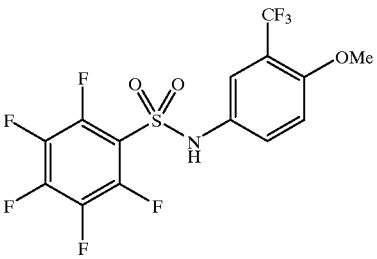

4-Methoxy-1-pentafluorophenylsulfonamido-3-trifluoromethylbenzene. The compound was prepared in a manner similar to that described in example 46 by replacing 3-chloroaniline with 4-methoxy-3-ifluoromethylaniline which was obtained by the hydrogenation of the corresponding nitro compound. White solid, mp 121–123° C. $^1$H NMR (CDCl$_3$): d 7.43–7.37(m, 2H), 6.96(d, J=8.8, 1H), 3.88(s, 3H). MS (EI): m/z 421(16, M$^+$), 190(100). Anal. Calcd. for $C_{14}H_7F_8NO_3S$: C, 39.92; H, 1.67; N, 3.32; S, 7.61. Found: C, 40.17; H, 1.68; N, 3.28; S, 7.67.

Example 50

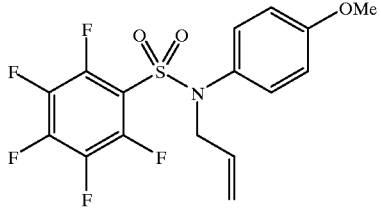

4-Methoxy-1-(N-(2-propenyl) pentafluorophenylsulfonamido)benzene. To a solution of 4-methoxy-1-pentafluorophenylsulfonamidobenzene (448 mg, 1.27 mmol) in THF (3 mL) was added triphenylphosphine (333 mg, 1.27 mmol) a,d alkyl alcohol (0.09 mL, 1.27 mmol). Diethylazodicarboxylate (0.20 mL, 1.27 mmol) was added and the mixture was stirred at rt After 1 h, the reaction mixture was poured onto saturated NaCl (10 mL) and extracted with $CH_2Cl_2$(3×10 mL). The combined organic extracts were washed with saturated $NaHCO_3$ (10 mL) and dried ($MgSO_4$). Concentration followed by flash chromatography (25:25:1/hexanes:$CH_2Cl_2$:EtOAc) provided 451 mg (90%) of product as a white solid, mp 59–60° C. $^1$H NMR ($CDCl_3$): d 7.06(m, 2H), 6.85(m, 2H), 5.79(m, 1H), 5.15(s, 1H), 5.11 (m, 1H), 4.37(d, J=6.3, 2H), 3.80(s, 3H). MS (EI): m/z 393(33, M$^+$), 162(100), 134(66). Anal. Calcd. for $C_{16}H_{11}F_5NO_3S$: C, 48.98; H, 2.83; N, 3.57; S, 8.17. Found: C, 49.13; H, 3.15; N, 3.63; S, 8.15.

Example 51

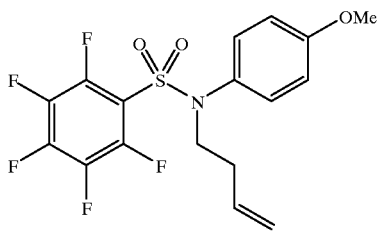

1-(N-(3-Butenyl)pentafluorophenylsulfonamido)-4-methoxybenzene. The compound was prepared in a manner similar to that described in example 50 by replacing alkyl alcohol with 3-buten-1-ol. White solid, mp 64–66° C. $^1$H NMR (CDCl3): d 7.08(m, 2H), 6.86(m, 2H), 5.74(m, 1H), 5.10–5.04(m, 2H), 3.83(m, 2H), 3.81(s, 3H), 2.25(q, J=6.9, 2H). MS (EI): m/z 407(13, M$^+$), 366(24), 135(100). Anal. Calcd. for $C_{17}H_{14}F_5NO_3S$: C, 50.13; H, 3.46; N, 3.44; S, 7.87. Found: C, 50.25; H, 3.51; N, 3.43; S, 7.81.

Example 52

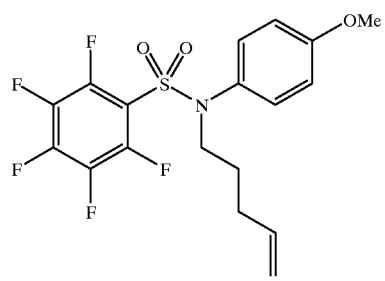

4-Methoxy-1-(N-(4-pentenyl) pentafluorophenylsulfonamido)benzene. The compound was prepared in a manner similar to that described in example 50 by replacing alkyl alcohol will 4-pentent-1-ol. Low melting semi-solid. $^1$H NMR ($CDCl_3$): d 7.08(m, 2H), 6.87(m, 2H), 5.74(m, 1H), 5.02–4.96(m, 2H), 3.81(s, 3H), 3.76(t, J=7.04, 2H), 2.11(q, J=6.9, 2H), 1.60(pentet, J=7.3, 2H). MS (EI): m/z 421(30, M$^+$), 190(100). Anal. Calcd. for $C_{18}H_{16}F_5NO_3S$: C, 51.31; H, 3.83; N, 3.32; S, 7.61. Found: C, 51.44; H, 3.89; N, 3.38; S, 7.54.

Example 53

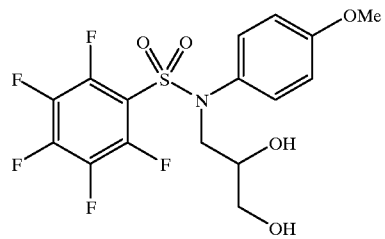

1-(N-2,3-Dihydroxypropyl) pentafluorophenylsulfonamido)-4-methoxybenzene. To a solution of 4-methoxy-1-(N-(2-propenyl) pentafluorophenyksulfonamido)benzene (101 mg, 0.26 mmol) in acetone:water (8:1, 1 mL) at rt was added N-methylmorpholine N-oxide (34.0 mg, 0.29 mmol) and $OsO_4$(0.10 mL of 0.16 M solution in $H_2O$, 1.60×10$^{-2}$ mmol). After stirring at rt for 18 h, the reaction mixture was treated with saturated $NaHSO_3$ (5 mL) and allowed to stir at rt. After 1 h, the reaction mixture was poured onto saturated $NAHSO_3$ (5 mL) and extacted with $CH_2Cl_2$ (3×10 mL). The combined organic extracts were dried ($MgSO_4$) and concentrated. Flash chromatography (1:1, 1:2/hexanes:EtOAc) afforded 90 mg (83%) of product as a white solid, mp 130–131° C. $^1$H NMR ($CDCl_3$): d 7.11(m, 2H), 6.85 (m, 2H), 3.78(s, 3H), 3.90–3.65(m, 5H). Anal. Calcd. for $C_6H_{13}F_5NO_5S$: C, 45.08; H, 3.07; N, 3.29; S, 7.52. Found: C, 45.09; H, 3.33; N, 3.27; S, 7.46.

Example 54

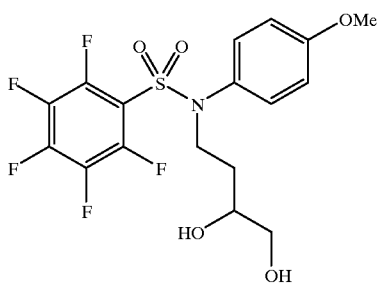

1-(N-(3,4-Dihydroxybutyl)pentafluorophenylsulfonamido)-4-methoxybenzene. The compound was prepared in a marner similr to that described in example 53 by replacing 4-methoxy-1-(N-(2-propenyl)pentafluorophenylsulfonaido)benzene with 1-(N-3-butenyl)pentafluorophenylsulfonamido)-4-methoxybenzene. White solid, mp 126–128° C. $^1$H NMR (CDCl$_3$): d 7.10(m, 2H), 6.88(m, 2M, 4.13(m, 1H), 3.96(m, 1H), 3.81(s, 3H), 3.78–3.73(m, 1H), 3.64(dd, 1, J=2.9, 10.7, 1H), 3.47(dd, J=7.3, 11.2; 1H), 2.67(bs, 1H), 1.92(bs, 1H), 1.62(m, 2H).

Example 55

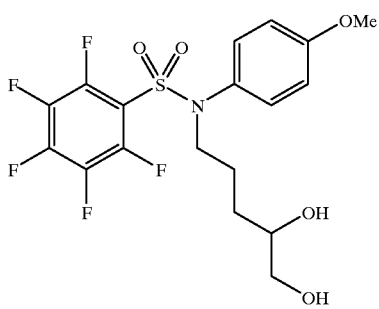

1-(N-(4,5-Dihydroxypentyl)pentafluorophenylsulfonamido)-4-methoxybenzene. The compound was prepared in a manner similar to that described in example 53 by replacing 4-methoxy-1-(N-(2-propenyl)pentafluorophenylsulfonamido)benzene with 4-methoxy-1-(N-(4-pentenyl)pentafluorophenylsulfonamido)benzene. White solid, mp 116–118° C. $^1$H NMR (CDCl$_3$): d 7.07(m, 2H), 6.86(m, 2H), 3.80(s, 3H), 3.78(m, 2H), 3.71–3.62(m, 2H), 3.43(dd, J=7.5, 10.8; 1H), 1.90(bs, 2H), 1.66–1.49(m, 4H). Anal. Calcd. for C$_{18}$H$_{18}$F$_5$NO$_5$S: C, 47.48; H, 3.98; N, 3.08; S, 7.04. Found: C, 47.58; H, 3.95; N, 3.06; S, 6.95.

Example 56

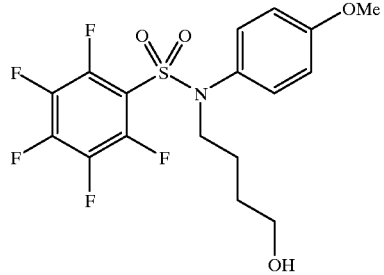

1-(N-(4-hydroxybutyl)pentafluorophenylsulfonamido)-4-methoxybenzene. To a solution of 1-(N-(3-butenyl)pentafluorophenylsulfonamido)-4-methoxybenzene (410 mg, 1.01 mmol) in THF (6.5 mL) at −78° C. was added BH$_3$.THF (1.00 mL of a 1 M solution in THF, 1.00 mmol). After stirring at −78° C. for 1 h and at 0° C. for 1 h, the reaction mixture was treated with H$_2$O (20 mL) and sodium perborate (513 mg, 5.14 mmol). After stirring at rt for 2 h, the mixture was poured onto H$_2$O (20 mL) and extracted with CH$_2$Cl$_2$ (3×15 mL). The combined organic extracts were washed with sat. NaCl (20 mL) and dried (MgSO$_4$). Concentration followed by chromatography (2:1/hexanes:EtOAc) afforded 270 mg (64%) of product as a white solid, mp 88–90° C. $^1$H NMR (CDCl$_3$): d 7.08(m, 2H), 6.85(m, 2H), 3.80(s, 3H), 3.77(m, 2H), 3.64(t, J=6.0; 2H), 1.63–1.55(m, 5H), 1.50(bs, 1H). Anal. Calcd. for C$_{17}$H$_{16}$F$_5$NO$_4$S: C, 48.00; H, 3.79; N, 3.29; S, 7.54. Found: C, 48.08; H, 3.76; N, 3.34; S, 7.46.

Example 57

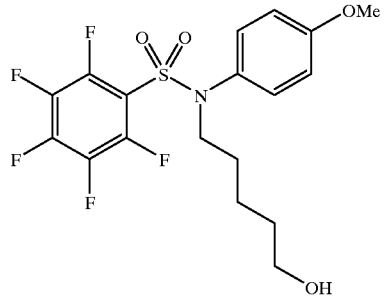

4-Methoxy-1-(N-(5-hydroxypentyl)pentafluorophenylsulfonamido)benzene. The compound was prepared in a manner similar to that described in example 56 by replacing 1-(N-(3-butenyl)pentafluorophenylsulfonamido)-4-methoxybenzene with 4-methoxy-1-(N(4-pentenyl)pentafluorophenylsulfonamido)benzene. White solid, mp 96–97° C. $^1$H NMR (CDCl$_3$): d 7.08(m, 2H), 6.86(m, 2H), 3.81(s, 3H), 3.76(t, J=6.8, 2H), 3.62(t, J=6.4; 2H), 1.58–1.43 (m, 6H). Anal. Calcd. for C$_{18}$H$_{18}$F$_5$NO$_4$S: C, 49.20; H, 4.13; N, 3.19; S, 7.30. Found: C, 49.11; H, 4.09; N, 3.14; S, 7.19.

Example 58

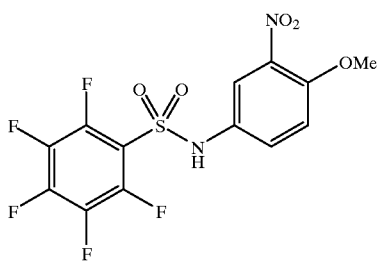

4-Methoxy-3-nitro-1-pentafluorophenylsulfonamidobenzene. The compound was prepared in a manner similar to example 46 by replacing 3-chloroaniline with 4-methoxy-3-nitroaniline which was prepared by the method of Norris (*Aust. J. Chem.* 1971,24, 1449). Orange-yellow solid, mp 95–97° C. $^1$H NMR (CDCl$_3$): d 7.64(d, J=2.7; 1H), 7.51(dd, J=2.7, 9.0; 1H), 7.09(s, 1H), 7.09(d, J=9.0; 1H), 3.95(s, 3H). Anal. Calcd. For C$_{13}$H$_7$F$_5$N$_2$O$_5$S: C, 39.21; H, 1.77; N, 7.03; S, 8.05. Found: C, 39.19; H, 1.73; N, 6.97; S, 7.95.

Example 59

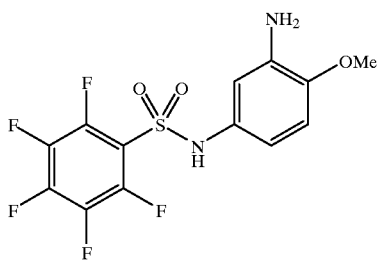

3-Amino-4-methoxy-1-pentafluorophenylsulfonamidobenzene. To a solution of 4-methoxy-3-nitro-1-pentafluorophenylsulfonamidobenzene (627 mg, 1.58 mmol) in ethanol (10 mL) was added 10% Pd/C (51 mg). The resulting mixture was stirred under an atmosphere of hydrogen gas at 1 atm pressure. After 14 h, the mixture was passed through a pad of celite and the filtte was concentrated to give a solid residue. Silica gel chromatography (2:1, 1:1/hexanes:EtOAc) yielded 542 mg (93%) of product as a white solid, mp 142–143° C. $^1$H NMR (DMSO-d$_6$): 10.64(s, 1), 6.68(d, J=8.4; 1H), 6.44(d, J=2.1; 1H), 6.30(d, J=2.1, 8.4; 1H), 4.88(bs, 2H), 3.69(s, 3H). Anal. Calcd. for C$_{13}$H$_9$F$_5$N$_2$O$_3$S: C, 42.40; H, 2.46; N, 7.61; S, 8.71. Found: C, 42.29; H, 2.36; N, 7.52; S, 8.60.

Example 60

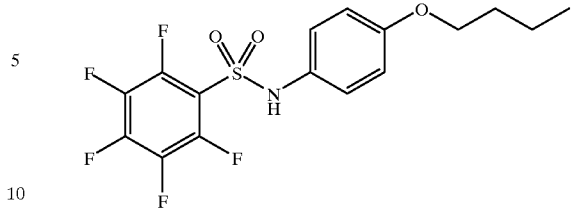

4-Butoxy-1-pentafluorophenylsulfonamidobenzene. To a solution of pentafluorophenylsulfonyl chloride (203 mg, 0.763 mmol) in MeOH (4 mL) was added 4-butoxyaniline (0.26 mL, 1.53 mmol). After stirring at rt for 1 h, the reaction mixture was poured onto 1 M HCl (15 mL) and extacted with CH$_2$Cl$_2$ (3×10 mL). The combined organic extracts were washed with saturated NaCl (10 mL) and dried (MgSO$_4$). Concentration followed by flash chromatography (25:25:1/hexanes: CH$_2$Cl$_2$:EtOAc) provided 189 mg (63%) of product $^1$H NMR (CDCl$_3$): d 7.07(m , 2H), 6.86(s, 1H), 6.80(m, 2H), 3.89(t, J=6.5; 2H), 1.73(m, 2H), 1.46(m, 21, 0.95(t, J=7.5; 2H). MS (EI): m/z 395(30, M$^+$), 164(35), 108(100). Anal. Calcd. for C$_{16}$H$_{14}$F$_5$NO$_3$S: C, 48.61; H, 3.57; N, 3.54; S, 8.11. Found: C, 48.54; H, 3.53; N, 3.50; S, 8.02.

Example 61

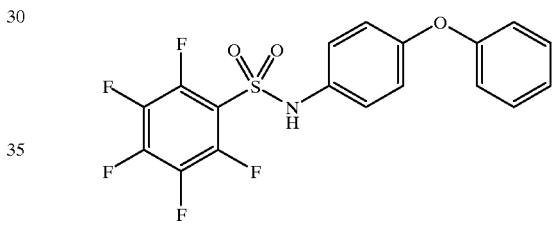

1-Pentafluorophenysulfonamido-4-phenoxybenzene. The compound was prepared in a manner similar to that described in example 60 by replacing 4-butoxyaniline with 4-phenoxyaniline. $^1$H NMR (CDCl$_3$): 7.36–7.30(m, 2H), 7.15–7.10(m, 3H), 6.99(s, 1H), 6.98–6.90(m, 4H). MS (EI): m/z 415(32, M$^+$), 184(100), 77(66). Anal. Calcd. for C$_{18}$H$_{10}$F$_5$NO$_3$S: C, 52.05; H, 2.43; N, 3.27; S, 7.72. Found: C, 51.78; H, 2.45; N, 3.25; S, 7.53.

Example 62

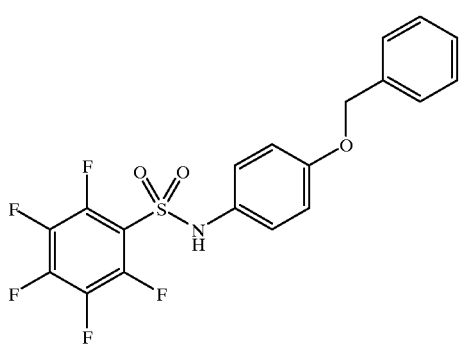

4-Benzyloxy-1-pentafluorophenylsulfonamidobenzene. The compound was prepared in a manner sirila to that described in example 60 by replacing 4-butoxyanilne with 4-benzyloxyauiline. 4-Benzyloxyailine was obtained from the commercially available hydrochloride salt by treatment with aqueous NaOH. $^1$H NMR (CDCl$_3$): 7.38–7.37(m, 4H), 7.36–7.32(m, 1H), 7.10–7.08(m, 2H), 7.91–7.88(m, 2H), 6.78(s, 1H), 5.01(s, 1H). MS (EI) m/z 429(19, M$^+$), 91(100). Anal. Calcd. for C$_{19}$H$_{12}$F$_5$NO$_3$S: C, 53.14; H, 2.82; N, 3.26; S, 7.45. Found: C, 53.07; H, 2.78; N, 3.21; S, 7.35.

Example 63

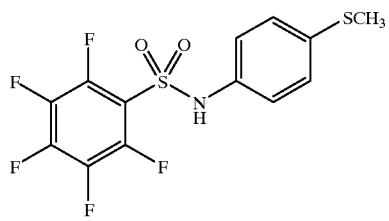

4-Methylmercapto-1-pentafluorophenylsulfonamidobenzene. The compound was prepared in a manner similar to that described in example 60 by replacing 4-butoxyailine with 4-(methylmercapto)ailine. $^1$H NMR (CDCl$_3$): 7.17(m, 2H), 7.09(m, 2H), 6.89(m, 1H), 2.44(s, 3H). MS (EI): m/z 369(24, M$^+$), 138(100), 77(66). Anal. Calcd. for C$_{13}$H$_8$F$_5$NO$_2$S$_2$: C, 42.28; H, 2.18; N, 3.79; S, 17.36. Found: C, 42.20; H, 2.21; N, 3.72; S, 17.28.

Example 64

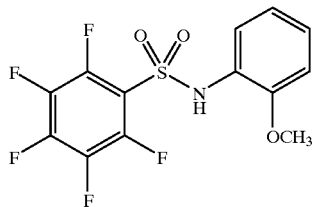

2-Methoxy-1-pentafluorophenylsulfonamidobenzene. The compound was prepared in a manner similar to that described in example 60 by replacing 4-butoxyaniline with o-anisidine $^1$H NMR (CDCl$_3$): d 7.54(dd, J=1.5, 8.0; 1H), 7.13(dt, J=1.5, 8.0; 1H), 6.94(dt, J=1.2, 8.0; 1H), 6.84(dd, J=1.2, 8.0; 1H), 3.79(s, 3H). MS (EI): m/z 353(82, M$^+$), 122(100), 94 (95). Anal. Calcd. for C$_{13}$H$_8$F$_5$NO$_3$S: C, 44.19; H, 2.28; N, 3.97; S, 9.06. Found: C, 44.10; H, 2.26; N, 3.92; S, 9.03.

Example 56

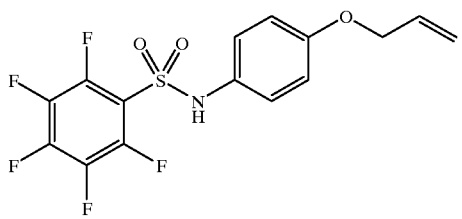

4-Allyloxy-1-pentafluorophenylsulfonamidobenzene. The compound was prepared in a anner similar to that described in example 60 by replacing 4-butoxyanilne with 4-alkyloxyanilie. 4-Allyloxyaniline was prepared by the method of Butera (J. Med. Chem. 1991, 34, 3212). $^1$H NMR (CDCl$_3$): 7.08(m, 2H), 6.87(m, 1H), 6.82(m, 2H), 6.04–5.94 (m, 1H), 5.39–5.34(m, 1H), 5.29–5.25(m, 1H), 4.484.46(m, 2H). MS (EI): m/z 379(11, M$^+$), 148(32), 41(100). Anal. Calcd. for C$_{15}$H$_{10}$F$_5$NO$_3$S: C, 47.50; H, 2.66; N, 3.96; S, 8.45. Found: C, 47.53; H, 2.68; N, 3.62; S, 8.37.

Example 66

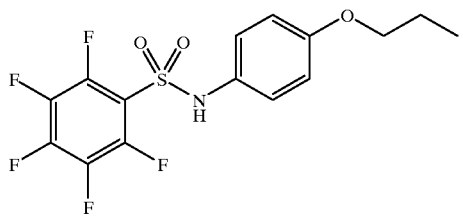

1-Penuruorophenylsulfonamido-4-propoxybenzene. The compound was prepared in a manner similar to that described in example 60 by replacing 4-butoxyaniline with 4-propoxyaniline. 4-Propoxyaniline was obtained by catalytic hydrogenation of 4-alkyloxynitrobenzene. 4-Allyloxynitrobenzene was prepared by the method of Butera (J. Med. Chem. 1991, 34, 3212). $^1$H NMR (CDCl$_3$): 7.09(m, 2H), 6.82(m, 2H), 6.78(m, 1H), 3.87(t, J=6.5; 2H), 1.78(m, 2H), 1.02(t, J=7.4; 3H). MS (El): m/z 381(20, M$^+$), 150 (40), 108(100). Anal. Calcd. for C$_{15}$H$_{12}$F$_5$NO$_3$S: C, 47.25; H, 3.17; N, 3.67; S, 8.41. Found: C, 47.01; H, 3.20; N, 3.61; S, 8.31.

Example 67

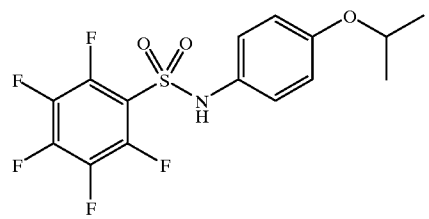

4-Methyl)ethoxy-1-pentafluorophenylsulfonamidobenzene. The compound was prepared in a manner similar to that described in example 60 by replacing 4-butoxyaniline with 4-isopropoxyaniline. 4-Isopropoxyaniline was prepared from 4-fluoronitrobenzene in analogy to the method of Day (J. Med. Chem. 1975, 18, 1065). $^1$H NMR (CDCl$_3$): 7.08(m, 2H), 7.00(s, 1H), 6.81(m, 2H), 4.48(heptet, J=6.1; 1H), 1.30(d, J=6.04; 6H). MS (EI): m/z 381(7, M$^+$), 339(8), 108(100). Anal. Calcd. for C$_{15}$H$_{12}$F$_5$NO$_3$S: C, 47.25; H, 3.17; N, 3.67; S, 8.41. Found: C, 47.08; H, 3.18; N, 3.60; S, 8.34.

Example 68

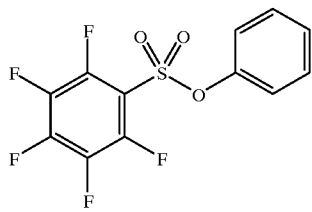

1-Pentafluorophenylsulfonyloxybenzene. To a stirred solution of phenol (0.068 g, 0.729 mmol) in dimethylfonnamide (3.65 mL) at 25° C. is added pentafluorophenyl sulfonyl chloride (0. 135 mL, 0.911 mmol), followed by sodium carbonate (0.116 g, 1.09 mmol), and the reaction mixture is stirred for 18 hours. The reaction mixture is diluted with ethyl acetate (50 mL), washed with 20% ammonium chloride (2×20 mL), and saturated sodium chloride (2×20 ml). The organic layer is dried (sodium sulfite), and the ethyl acetate removed under vacuum. Column chromatography (3/1 ethyl acetatelhexane) yields the title compound.

Example 69

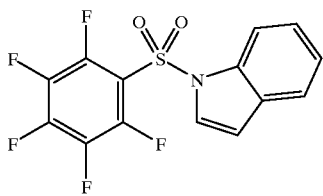

1-Pentafluorophenylsulfonylindole. To a stirred solution of indole.(0.085 g, 0.729 mmol) in dimethylformamide (3.65 mL) at 25° C. is added pentafluorophenyl sulfonyl chloride (0.135 mL, 0.911 mmol), followed by sodium carbonate (0.116 g, 1.09 mmol), and the reaction mixture is stirred for 18 hours. The reaction mixture is diluted with ethyl acetate (50 mL), washed with 20% ammonium chloride (2×20 mL), and saturated sodium chloride (2×20 mL). The organic layer is dried (sodium sulfite), and the ethyl acetate removed under vacuum. Column chromatography (3/1 ethyl acetate/hexane) yields the title compound.

Example 70

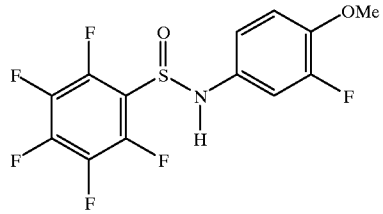

2-Fluoro-1-methoxy-4-pentafluorophenylsulfonamidobenzene. To 3-fluoro-p-anisidine (3 g 21.2 mmol) suspended in THF (50 mL) with pyridine (1.84 g, 23.3 mmol) at 0° C. under argon is added dropwise pentafluorophenylsulfinyl chloride (5.3 g, 21.2 mmol). The reaction mixture is stirred for 30 min. at 0° C. and allowed to warm to ambient temperature. The reaction mixture is strirred at room temperature and followed by TLC. After the reaction is completed the mixture is diluted with ethyl acetate and the reaction quenched with water. The layers are separated and the aqueous layer extracted twice with ethyl acetate. The organic layers are combined and dried with brine and with $Na_2SO_4$. The solvent is evaporated and the residue purified by chromatography on silica to give the title compound.

Example 71

2-Anilino-3-pentafluorophenylsulfonamidopyridine. To a solution of pentafluorophenyisulfony chloride (863 mg, 3.24 mmol) in pyridine (9 mL) at rt was added 3-amino-2-analinopyridine (600 mg, 3.24 mmol). After stirring at rt overnight the reaction mixture was concented at reduced pressure and the residue partitioned between 1 M Hcl (50 mL) and CH2Cl2 (50 mL). The organic extract was dried and concentrated to give an oil which was purified by MPLC to give 377 mg (28%) of product as an orange solid. $H^1$ NMR ($CDCl_3$): 8.50(bs, 1H), 7.80(d, J=5.1, 1H), 7.61(d, J=8.0, 1H), 7.32(t, J=8.0, 2H), 7.25(d, J=8.0, 2H), 7.11(t, J=7.3, 1H), 6.80(dd, J=5.6, 7.7, 1H), 4.20(bs, 1H). MS (FAB): m/z 438 ($M^{+Na}$), 416(M+H).

Example 72

Compounds were evaluated for their ability to increase LDL receptor expression in Hep G2 cells using western-blot analysis as described in Tam et al., J. Biol. Chem., 266, 16764 (1991) The data presented ($EC_{max}$) reflect the minimum concentration at which a maximal induction of LDL receptor was observed for each compound. In all cases, the level of induction was greater than that observed under lipid-free conditions (activated system).

| Compound | $EC_{max}$ ($\mu$m) |
|---|---|
| Example 1 | 0.5 |
| Example 2 | 5 |
| Example 3 | 5 |
| Example 4 | ≦5 |
| Example 6 | 0.15 |
| Example 7 | 0.5 |
| Example 8 | 0.5 |
| Example 9 | 5 |
| Example 12 | 5 |
| Example 15 | 15 |
| Example 17 | 5 |
| Example 24 | 15 |
| Example 25 | 15 |
| Example 30 | 15 |
| Example 31 | ≦5 |
| Example 32 | 1.5 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical composition comprising a pharmaceutically acceptable excipient and a compound of the formula:

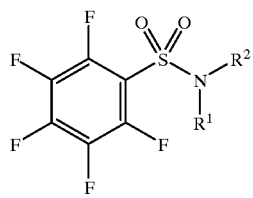

wherein
   $R^1$ is selected from hydrogen and substituted or unsubstituted $(C_1-C_{10})$alkyl; and
   $R^2$ is substituted or unsubstituted naphthyl.

2. The pharmaceutical composition of claim 1, wherein said compound is 7-hydroxy-2-pentafluorophenylsulfonamidonaphthalene.

3. A method of treating or preventing a disease state characterized by abnormally high levels of low density lipoprotein particles or cholesterol in the blood, comprising administering to a mammalian subject in need thereof a therapeutically effective amount of a compound of the formula:

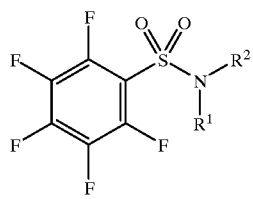

wherein
   $R^1$ is selected from hydrogen and substituted or unsubstituted $(C_1-C_{10})$alkyl; and
   $R^2$ is substituted or unsubstituted naphthyl.

4. The method of claim 3, wherein said disease state is atherosclerosis.

5. The method of claim 3, wherein said disease state is pancreatitis.

6. The method of claim 3, wherein said disease state is hypercholesterolemia.

7. The method of claim 3, wherein said disease state is hyperlipoproteinemia.

8. The method of claim 3, wherein said composition is administered orally.

9. The method of claim 3, wherein said subject is a human.

10. The method of claim 3, wherein said compound is administered in combination with a therapeutically effective amount of a hypolipemic agent or a hypocholesterolemic agent.

11. A compound having the formula:

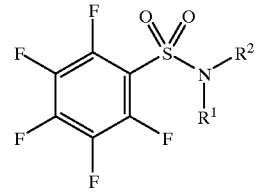

or a pharmaceutically acceptable salt thereof, wherein
   $R^1$ is selected from hydrogen and substituted or unsubstituted $(C_1-C_{10})$alkyl; and
   $R^2$ is substituted or unsubstituted naphthyl; with the proviso that when $R^1$ is hydrogen, $R^2$ is substituted naphthyl;
   wherein said compound has pharmacological activity.

12. The compound of claim 11, wherein said compound is 7-hydroxy-2-pentafluorophenylsulfonamidonaphthalene.

13. A compound having the formula:

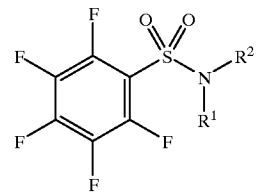

or a pharmaceutically acceptable salt thereof, wherein
   $R^1$ is substituted or unsubstituted $(C_1-C_{10})$alkyl; and
   $R^2$ is substituted or unsubstituted naphthyl.

14. The compound of claim 13, wherein said compound is 7-hydroxy-2-pentafluorophenylsulfonamidonaphthalene.

* * * * *